US 8,231,602 B2

(12) United States Patent
Anderson et al.

(10) Patent No.: US 8,231,602 B2
(45) Date of Patent: Jul. 31, 2012

(54) METHOD OF CLEANING AND COVERING AN ACCESS SITE

(75) Inventors: William Anderson, Cary, IL (US); Mark Wilson, Rochester, NY (US); Gary Henniger, Belmar, NJ (US); Larry Colquitt, West Henrietta, NY (US); Christopher E. Gardner, Manalapan, NJ (US)

(73) Assignee: Excelsior Medical Corporation, Neptune, NJ (US)

( * ) Notice: Subject to any disclaimer, the term of this patent is extended or adjusted under 35 U.S.C. 154(b) by 0 days.

(21) Appl. No.: 13/095,516

(22) Filed: Apr. 27, 2011

(65) Prior Publication Data

US 2011/0290799 A1   Dec. 1, 2011

Related U.S. Application Data

(63) Continuation of application No. 12/214,526, filed on Jun. 19, 2008, which is a continuation-in-part of application No. 11/821,190, filed on Jun. 22, 2007, now Pat. No. 8,167,847.

(60) Provisional application No. 60/815,806, filed on Jun. 22, 2006.

(51) Int. Cl.
*A61M 31/00*   (2006.01)
*A61M 5/00*   (2006.01)

(52) U.S. Cl. ........................................ 604/513; 604/187

(58) Field of Classification Search .................. 604/187, 604/500, 513
See application file for complete search history.

(56) References Cited

U.S. PATENT DOCUMENTS

| 877,946 | A | | 2/1908 | Overton |
|---|---|---|---|---|
| 3,270,743 | A | | 9/1966 | Gingras |
| 3,977,401 | A | | 8/1976 | Pike |
| 4,041,934 | A | | 8/1977 | Genese |
| 4,243,035 | A | | 1/1981 | Barrett |
| 4,317,446 | A | | 3/1982 | Ambrosio et al. |
| 4,335,756 | A | | 6/1982 | Sharp et al. |
| 4,402,691 | A | | 9/1983 | Rosenthal et al. |
| 4,417,890 | A | | 11/1983 | Dennehey et al. |
| 4,432,764 | A | | 2/1984 | Lopez |
| 4,432,766 | A | | 2/1984 | Bellotti et al. |
| 4,439,184 | A | | 3/1984 | Wheeler |
| 4,440,207 | A | * | 4/1984 | Genatempo et al. .......... 150/154 |
| 4,507,111 | A | | 3/1985 | Gordon et al. |
| 4,624,664 | A | | 11/1986 | Peluso et al. |

(Continued)

FOREIGN PATENT DOCUMENTS

CA   2 583 601   4/2006

(Continued)

OTHER PUBLICATIONS

Examination Report dated Jun. 6, 2011, issued by the Canadian Intellectual Property Office in connection with Canadian Patent Application No. 2,692,157 (2 pages).

(Continued)

*Primary Examiner* — Kevin C Sirmons
*Assistant Examiner* — Bradley Osinski
(74) *Attorney, Agent, or Firm* — McCarter & English, LLP

(57) ABSTRACT

A syringe assembly including: (1) a syringe barrel defining a chamber; (2) a plunger mounted in the chamber and moveable with respect to the barrel; and (3) a cap assembly containing a cap and an absorbent material is removably attached to the plunger.

13 Claims, 16 Drawing Sheets

U.S. PATENT DOCUMENTS

| | | | |
|---|---|---|---|
| 4,671,306 | A | 6/1987 | Spector |
| 4,703,762 | A | 11/1987 | Rathbone et al. |
| 4,728,321 | A | 3/1988 | Chen |
| 4,778,447 | A | 10/1988 | Velde et al. |
| 4,799,926 | A | 1/1989 | Haber |
| 4,811,847 | A | 3/1989 | Reif et al. |
| 4,957,637 | A | 9/1990 | Cornell |
| 4,983,161 | A | 1/1991 | Dadson et al. |
| 4,989,733 | A * | 2/1991 | Patry .............................. 206/570 |
| 5,190,534 | A | 3/1993 | Kendell |
| D342,134 | S | 12/1993 | Mongeon |
| 5,554,135 | A | 9/1996 | Menyhay |
| 5,792,120 | A | 8/1998 | Menyhay |
| 5,820,604 | A | 10/1998 | Fox et al. |
| 5,827,244 | A | 10/1998 | Boettger |
| 5,954,957 | A | 9/1999 | Chin-Loy et al. |
| 5,989,229 | A | 11/1999 | Chiappetta |
| 6,045,539 | A | 4/2000 | Menyhay |
| 6,116,468 | A | 9/2000 | Nilson |
| 6,126,640 | A | 10/2000 | Tucker et al. |
| 7,431,712 | B2 | 10/2008 | Kim |
| 635,344 | A1 | 12/2009 | Tennican et al. |
| D607,325 | S | 1/2010 | Rogers et al. |
| 7,731,678 | B2 | 6/2010 | Tennican et al. |
| 7,731,679 | B2 | 6/2010 | Tennican et al. |
| 7,749,189 | B2 | 7/2010 | Tennican et al. |
| 7,753,891 | B2 | 7/2010 | Tennican et al. |
| 7,763,006 | B2 | 7/2010 | Tennican |
| 7,776,011 | B2 | 8/2010 | Tennican et al. |
| 7,780,794 | B2 | 8/2010 | Rogers et al. |
| 7,799,010 | B2 | 9/2010 | Tennican |
| 7,857,793 | B2 | 12/2010 | Raulerson et al. |
| 7,922,701 | B2 | 4/2011 | Buchman |
| 2004/0258560 | A1 | 12/2004 | Lake, Jr. et al. |
| 2005/0013836 | A1 | 1/2005 | Raad |
| 2005/0065479 | A1 * | 3/2005 | Schiller et al. ................ 604/218 |
| 2005/0147524 | A1 | 7/2005 | Bousquet |
| 2005/0203460 | A1 | 9/2005 | Kim |
| 2006/0030827 | A1 | 2/2006 | Raulerson et al. |
| 2007/0112333 | A1 | 5/2007 | Hoang et al. |
| 2007/0167910 | A1 | 7/2007 | Tennican et al. |
| 2007/0249996 | A1 | 10/2007 | Tennican et al. |
| 2007/0265578 | A1 | 11/2007 | Tennican et al. |
| 2007/0282280 | A1 | 12/2007 | Tennican |
| 2008/0086091 | A1 | 4/2008 | Anderson et al. |
| 2009/0012426 | A1 | 1/2009 | Tennican |
| 2009/0093757 | A1 | 4/2009 | Tennican |
| 2009/0099529 | A1 | 4/2009 | Anderson et al. |
| 2010/0160894 | A1 | 6/2010 | Julian et al. |

FOREIGN PATENT DOCUMENTS

| | | |
|---|---|---|
| CA | 2 626 864 | 5/2007 |
| CA | 2 651 192 | 11/2007 |
| EP | 0227219 | 7/1987 |
| WO | WO 2004/112846 A2 | 12/2004 |
| WO | WO 2007/137056 A2 | 11/2007 |
| WO | WO 2009/002474 | 12/2008 |

OTHER PUBLICATIONS

Examination Report dated Jun. 13, 2011, issued by the Intellectual Property Office of New Zealand in connection with New Zealand Patent Application No. 582395 (2 pages).

Interview Summary dated Nov. 18, 2010, from pending U.S. Appl. No. 11/821,190 (5 pages).

Office Action dated Dec. 17, 2009 from U.S. Appl. No. 11/821,190 (10 pages).

Office Action dated Aug. 2, 2010 from U.S. Appl. No. 11/821,190 (14 pages).

Office Action dated Mar. 7, 2011 from U.S. Appl. No. 11/821,190 (16 pages).

Notice of Allowance dated Apr. 26, 2011 from U.S. Appl. No. 11/821,190 (9 pages).

International Search Report of the International Searching Authority mailed Sep. 11, 2008, issued in connection with International Patent Appln. No. PCT/US08/07797 (2 pages).

Written Opinion of the International Searching Authority mailed Sep. 11, 2008, issued in connection with International Patent Appln. No. PCT/US08/07797 (3 pages).

Office Action mailed Jun. 9, 2011 from U.S. Appl. No. 12/214,526 (8 pages).

Redacted version of letter from David A. Divine, Esq. of Lee & Hayes, dated May 27, 2011 (3 pages).

Redacted version of letter from David A. Divine, Esq. of Lee & Hayes, dated May 16, 2011 (3 pages).

Notice of Allowance dated Jul. 29, 2011, from U.S. Appl. No. 11/821,190 (6 pages).

Notification of First Office Action dated Aug. 3, 2011, issued by the State Intellectual Property Office of the People's Republic of China in connection with Chinese Patent Application No. 200880103854.5 (5 pages).

Office Action mailed Oct. 31, 2011 from U.S. Appl. No. 12/214,526 (9 pages).

Photographs of the Baxter Minicap (4 pages) (product sold at least one year prior to the earliest filing date).

Examiner's Report dated Mar. 29, 2012, issued by the Canadian Intellectual Property Office in connection with Canadian Patent Application No. 2,692,157 (3 pages).

Second Office Action dated Mar. 29, 2012, along with English translation, issued by the State Intellectual Property Office of the People's Republic of China in connection with Chinese Patent Application No. 200880103854.5 (7 pages).

* cited by examiner

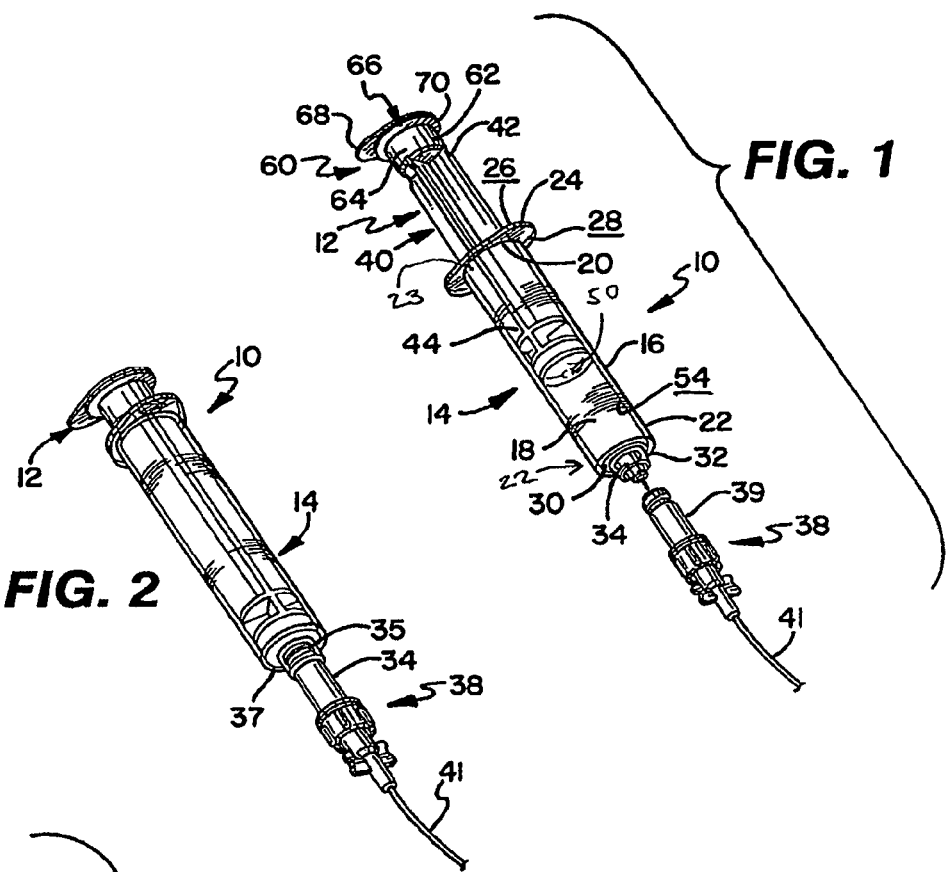
FIG. 1
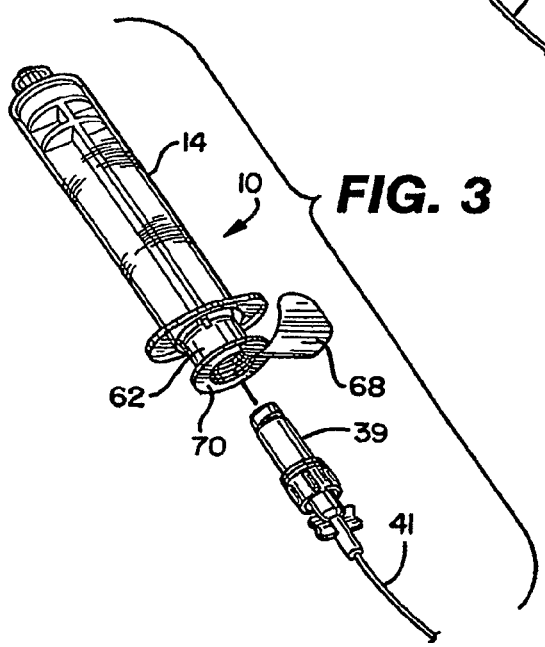
FIG. 2
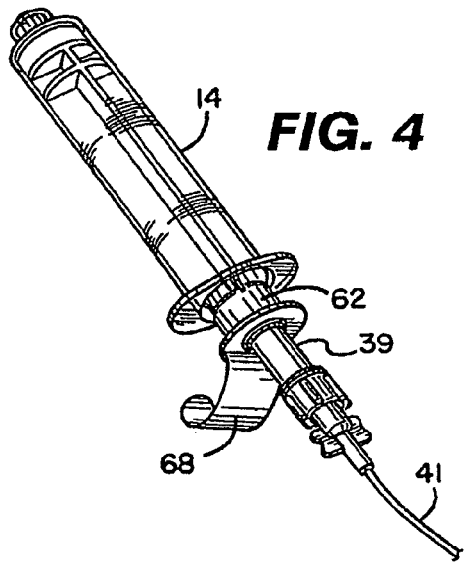
FIG. 3
FIG. 4

METHOD OF CLEANING AND COVERING AN ACCESS SITE

CROSS-REFERENCE TO RELATED APPLICATIONS

This application is a continuation of U.S. patent application Ser. No. 12/214,526, filed on Jun. 19, 2008, which is a continuation-in-part of U.S. application Ser. No. 11/821,190 filed on Jun. 22, 2007, now U.S. Pat. No. 8,167,847, which claims the benefit of U.S. Provisional Application Ser. No. 60/815,806 filed on Jun. 22, 2006, the entire disclosures of which are all expressly incorporated herein by reference, and this application is a continuation-in-part of U.S. application Ser. No. 11/821,190 filed on Jun. 22, 2007, now U.S. Pat. 8,167,847, which claims the benefit of U.S. Provisional Application Ser. No. 60/815,806 filed on Jun. 22, 2006.

BACKGROUND OF THE INVENTION

1. Technical Field

The present invention relates to an antiseptic cap having a thread cover to enhance a seal between the cap and an access site to a body of a mammal. More particularly the invention relates to an antiseptic cap for attaching to an access site of an indwelling, central venous catheter and having a thread cover to enhance a seal between the cap and the access site.

2. Background Art

Catheters are widely used to treat patients requiring a variety of medical procedures. Catheters can either be acute, or temporary, for short-term use or chronic for long-term treatment. Catheters are commonly inserted into central veins (such as the vena cava) from peripheral vein sites to provide access to a patient's vascular system. Catheters offer many advantages for patients; for example, chronic catheters provide ready access without repeated punctures or repeated vessel cannulation for administration of large volumes of fluids, nutrients and medications and for withdrawal of blood on an intermittent basis. With respect to the use of catheters for infusion of fluids, examples include the infusion of drugs, electrolytes or fluids used in chemotherapy. In chemotherapy, catheters are used for infusion of drugs on an intermittent basis, ranging from daily to weekly. Another example includes the use of catheters in hyperalimentation treatment, wherein the catheters are usually used for infusion of large volumes of fluids.

For hemodialysis, catheters are commonly used—usually three times per week—for aspiration of blood for dialysis treatment and rapid return of the blood to circulation after treatment. Although a preferred mode of vascular access for a hemodialysis patient involves using an arteriovenous (AV) fistula of either the upper or lower extremities or an arteriovenous "bridge" graft (typically utilizing PTFE), use of these access devices is not always possible or desirable. When either of these modes of vascular access is not available, for example, due to a paucity of adequate blood vessels for creation of AV "shunts" or due to nonoptimally functioning established AV shunts, a large bore venous line catheter is typically required for hemodialysis. Catheters used for hemodialysis usually include two relatively large diameter lumens (usually molded as one catheter) for aspiration and rapid return of blood required during the hemodialysis procedure. One lumen of such a catheter is used for aspiration, or removal, of blood, while the other lumen is used for returning the blood to the patient's bloodstream.

Catheter connections, such as, for example, connections of catheters to dialysis machine tubing, to IV line tubing, to infusion ports and to catheter caps, which are used to seal the end of a catheter to protect the sterility of the catheter and prevent fluid loss and/or particle contamination, are most often made utilizing the medical industry's standardized Luer taper fittings. These fittings, which may either be male couplings or female couplings, include a tapered end of standardized dimensions. Coupling is made by the press-fit of mating parts. A threaded lock-fit or other type of securing mechanism is commonly utilized to ensure the integrity of the pressure fit of the Luer fittings.

Catheters, especially chronic venous catheters, provide challenges in their use. One such challenge is that such catheters can become occluded by a thrombus. In order to prevent clotting of catheters in blood vessels between uses, such as, for example, between dialysis treatments when the catheter is essentially nonfunctioning and dwells inside a "central" vein (i.e. superior vena cava, inferior vena cava, iliac, etc), the lumens of the catheter are often filled with a lock solution of a concentrated solution of the commonly used anticoagulant, heparin (up to 10,000 units of heparin per catheter lumen).

As used herein, the terms "lock solution" or "locking solution" refer to a solution that is injected or otherwise infused into a lumen of a catheter with the intention of allowing a substantial portion of the lock solution to remain in the lumen and not in the systemic blood circulation until it is desired or required to access that particular lumen again, typically for additional treatment, i.e., infusion or withdrawal of fluid. In addition, attention has been given to the development of alternative lock solutions with the goal of improving the patency rates of vascular catheters. For example, lower-alcohol containing locking solutions are under development wherein the lower alcohols include ethanol, propanol and butanol. Antimicrobial and or anticoagulant additives can optionally be added to the lower-alcohol containing locking solution. Preferably the lock solution can remain in the lumen for a desired amount of time lasting from about 1 hour to 3 or 4 days or longer.

For the reasons set forth above, significant care must be taken when infusing medications, nutrients and the like into a catheter, and when "locking" a catheter between uses, to minimize the risks associated with an indwelling catheter, including the risk of thrombosis or clotting, the risk of excessive anticoagulating and the risk of infection. Syringes are typically used to administer the required amount of catheter lock solution (determined by the catheter manufacturer) into an indwelling catheter after a given use. Flush procedures also require that care be taken to prevent blood reflux into the catheter. Reflux in I.V. therapy is the term commonly used to describe the fluid that is drawn back into the catheter after a flush procedure. The concern is that the reflux fluid contains blood or solution that could cause the catheter to occlude. To ensure that reflux does not occur, flush procedures suggest two techniques: 1) at the end of the flush solution delivery, the user maintains pressure on the syringe plunger while clamping the I.V. line; or 2) while delivering the last 0.5 ml of flush solution disconnect the syringe from the I.V. port or clamp the IV. line. Either technique maintains positive pressure on the fluid in the catheter to prevent reflux of fluid and blood.

In light of the above-described problems, there is a continuing need for advancements in catheter lock techniques, devices and procedures to improve the safety and efficacy of catheter locking procedures and of overall patient care.

BRIEF DESCRIPTION OF THE DRAWINGS

FIG. 1 is a perspective view of an antiseptic cap equipped plunger and syringe barrel assembly prior to connection of a syringe tip to an access point to a central venous catheter;

FIG. 2 is a perspective view of an antiseptic cap equipped plunger and syringe barrel assembly with the syringe tip connected to an access point to a central venous catheter;

FIG. 3 is a perspective view of an antiseptic cap equipped plunger and syringe barrel assembly prior to connection of the antiseptic cap to an access point to a central venous catheter;

FIG. 4 is a perspective view of an antiseptic cap equipped plunger and syringe barrel assembly after connection of the antiseptic cap to an access point to a central venous catheter;

DETAILED DESCRIPTION OF THE INVENTION

Figure 5:
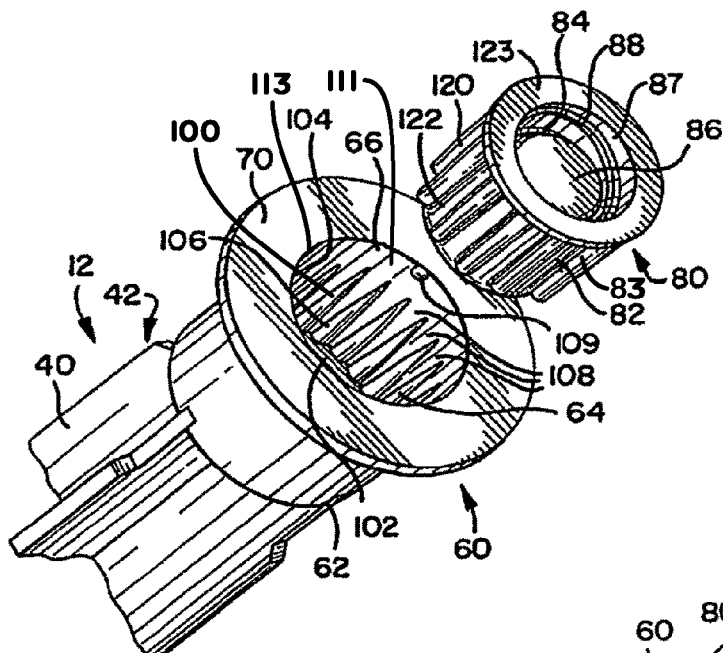
FIG. 5 is a perspective view assembly drawing of an antiseptic cap equipped plunger.

While this invention is susceptible of embodiment in many different forms, there is shown in the drawings, and will be described herein in detail, specific embodiments thereof with the understanding that the present disclosure is to be considered as an exemplification of the principles of the invention and is not intended to limit the invention to the specific embodiments illustrated.

FIGS. 1 and 2 show an antiseptic cap equipped plunger and syringe barrel assembly 10 having an antiseptic cap equipped plunger (or piston) assembly 12 and a syringe barrel 14. The barrel 14 has a side wall 16 defining a chamber 18 and the barrel has a proximal end 20 and a distal end 22. The proximal end 20 has an opening 23 to the chamber 18 and a flange 24 extending radially outwardly from the wall 16. The flange 24 has upper and lower surfaces 26, 28 and provides gripping surfaces for a user of the assembly 10. The distal end 22 of the barrel 14 has an end wall 30 and an elongate tip 32 extending distally therefrom and having a passageway 34 therethrough and in fluid communication with the chamber 18. The distal end wall 30, in one preferred form of the invention, is generally conically shaped and, as is well known in the art, can have a locking luer collar 35 concentrically surrounding the tip 32 and having a set of threads 37 on an inside surface thereof. The luer collar 35 allows for attaching a needle or a cannula to barrel 14 and for docking the assembly 10 to mating threads located on other devices such as valves, injection sites and other medical access devices well known in the art. FIG. 1 shows the syringe assembly proximate an access site 38 having a valve 39 controlling access to a lumen of a tubing 41.

In one preferred form of the invention the chamber 18 of the syringe assembly 10 will be filled with a locking solution or a flush solution for use with an indwelling, central venous catheter. The manner of using a locking or flush solution with a catheter is well known in the art. Suitable locking or flushing solutions will be set forth below. The flush or locking solution is injected into a fluid access site of the catheter to clean and disinfect the catheter and can be withdrawn from the catheter or allowed to remain in an end portion of the catheter to serve as a barrier to the ingress of pathogens and contaminants.

The antiseptic cap plunger assembly 12 has an elongate shaft 40, a proximal end 42 and a distal end 44. The elongate shaft 40, in one preferred form of the invention, is generally cruciform in cross-sectional shape. A stopper or piston 50 is connected to the distal end 44 of the plunger 40. The piston 50 is dimensioned such that when inserted into the syringe barrel chamber 18 an outer circumferential surface of the piston 50 is in fluid-tight engagement with an inner surface 54 of the syringe barrel. The piston assembly 14 when moved proximally (or when being withdrawn) can draw fluid into the chamber and when moved distally (or when inserted into the syringe chamber) can drive fluid out of the chamber. FIG. 1 shows the piston assembly 12 partially inserted into the syringe chamber and FIG. 2 shows the piston assembly fully inserted into the syringe chamber to deliver fluid to the tubing 41.

A housing 60 is located at the proximal end 42 of the plunger assembly 12 and has a wall 62 defining a chamber 64 having an open end 66 which can be sealed by any suitable structure or material such as a cap or by a foil material 68. An optional annular flange 70 extends radially outwardly from the wall 62 and provides a surface upon which the sealing structure can be attached.

Figure 6:
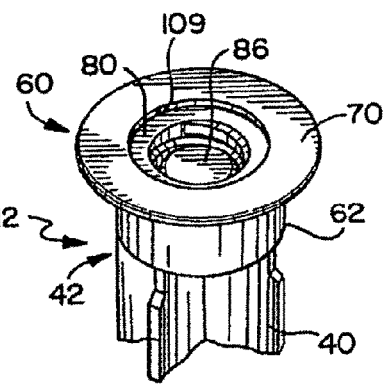
FIG. 6 is a perspective view of an antiseptic cap equipped plunger in a partially assembled state.

FIG. 5 shows a cap assembly 80 proximate the chamber 64 of the housing 60 and FIG. 6 shows the cap assembly 80 positioned within the chamber 64. In one preferred form of the invention, the cap assembly 80 has a cap 82 having a wall 83 defining a chamber 84 containing an absorbent material 86 such as a sponge. The sponge 86, in a preferred form of the invention, is wetted or soaked with an agent such as an antiseptic, anticoagulant or antimicrobial ("antiseptic solution") and can be selected from the locking and flushing solutions set forth below or the antiseptic solutions set forth below. The cap 82 has an interior surface 87 with a set of threads 88 for mating with a set of threads on the access site 38.

Figure 7:
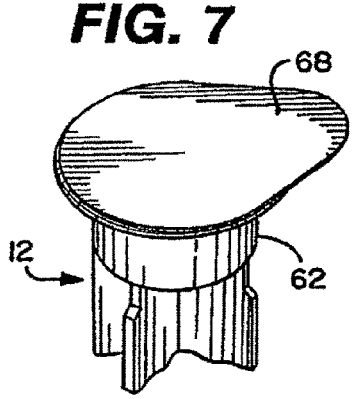
FIG. 7 is a perspective view of the antiseptic cap equipped plunger of FIG. 6 with a top seal.
Figure 8:
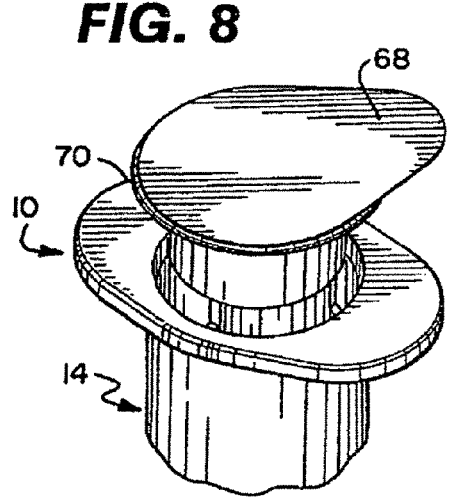
FIG. 8 is a perspective view of an antiseptic cap equipped plunger of FIG. 7 mounted in a lumen of a syringe barrell.
Figure 9:
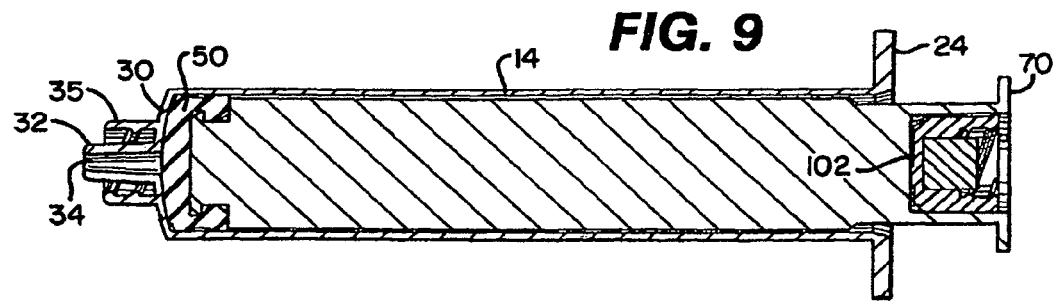
FIG. 9 is a side view in cutaway of an antiseptic cap equipped plunger and syringe barrel assembly.
Figure 10:
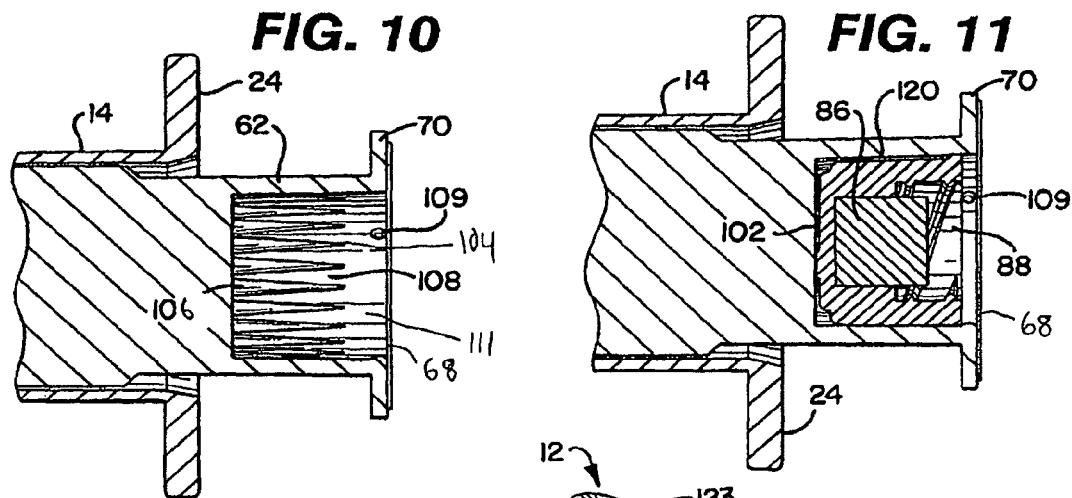
FIG. 10 shows an exploded view of a detail of FIG. 9 of one embodiment of the antiseptic cap equipped plunger and syringe barrel assembly.

FIGS. 7 and 8 show the cap assembly 80 sealed with a foil material or lid stock material 68 which can be attached to the flange 70 by any suitable method such as by adhesives or by conductive or inductive heat sealing techniques. FIG. 7 shows the antiseptic cap piston assembly 12 and FIG. 8 shows the antiseptic cap equipped piston assembly 12 inserted into the chamber of the syringe barrel 14 to define the antiseptic cap equipped piston and syringe barrel assembly 10.

FIGS. 3 and 4 show one possible method for utilizing the cap assembly 80 by docking with the access device 38. FIG. 3 shows the lid stock 68 pealed away from the flange 70 and FIG. 4 shows docking the antiseptic cap assembly 80 to the valve 39. The syringe barrel is rotated clockwise or counter-clockwise to engage the threads 88 of the antiseptic cap assembly 80 with the threads of the access site 38. After engagement, the syringe barrel 14 will be moved away from the access site 38 and the antiseptic cap assembly 80 will slide outward from the housing 60 and remain docked to the access site 38. The antiseptic cap assembly 80 can remain docked to the valve 39 of the access site 38 for any suitable period of time from a few minutes to numerous hours. When the antiseptic cap assembly 80 is docked to the valve 39 the tubing or catheter 41 is sealed to block the ingress into the catheter of pathogens and contaminants and a portion of the access site 38 is exposed to the antiseptic material in the sponge 86.

It is desirable that during the rotation of the syringe barrel that the antiseptic cap assembly 80 does not rotate with respect to the housing and/or optionally that the plunger assembly 12 does not rotate with respect to the syringe barrel 14 until the threads 88 of the antiseptic cap can fully engaged the threads of the access site 38. The present invention provides a mechanism associated with the assembly 10 for preventing the rotation of the antiseptic cap assembly 80 with respect to the plunger assembly 12 and more preferably a mechanism on either the plunger assembly or on the antiseptic cap 80 to prevent relative rotational movement between the antiseptic cap 80 and the plunger assembly 12. In an even more preferred form of the invention, the mechanism for preventing relative rotation of the antiseptic cap assembly 80 with respect to the plunger assembly 12 has mating portions on both parts that when assembled cooperatively engage one another to prevent relative rotation. It is also contemplated that a separate mechanism, device or member could be used to lock the two parts together to achieve this purpose.

If a user grasps the assembly 10 by the antiseptic cap and plunger assembly 12 than the interlocking structures between the plunger assembly 12 and the syringe barrel 14 would not necessarily be needed. Accordingly, FIGS. 5, 9-11 show exemplary structures for locking the antiseptic cap assembly 80 inside the housing 60 so that these parts rotate together and one part does not rotate in a direction or at a rate different from that of the other part. Further, FIGS. 15-18 show exemplary structures for interlocking the antiseptic cap plunger assembly 12 with the syringe barrel 14.

In one preferred form of the invention the housing 60 will have a feature or structure that forms an interference fit with an external surface 83 of the antiseptic cap 80. Even more preferably, an internal surface 63 of the side wall 62 of the housing 60 will have a feature or structure to form an interference fit with a portion of the antiseptic cap assembly 80. In another preferred form of the invention the antiseptic cap assembly 80 will have a feature to form an interference fit with the housing 60 and even more preferably the outer surface 83 of the antiseptic cap 80 will have a feature to contact the inner surface 63 of the housing side wall 62.

In another preferred form of the invention the plunger housing 60 and the cap assembly 80 each will have a feature or structure that cooperatively engage one another to prevent relative rotation of the cap assembly 80 and the housing 60. FIG. 5 shows one preferred form of the invention having a plurality of circumferentially spaced and axially extending ribs 100 on the internal surface 63 of the housing side wall 62 (internal ribs 100) for engaging the wall 83 of the antiseptic cap 82 to lock the cap assembly 80 in place to prevent rotation of the cap assembly 80 when positioned inside the housing 60. In a preferred form of the invention, the internal ribs 100 extend from a bottom wall 102 up to an intermediate height of the housing sidewall 62. In a preferred form of the invention the internal ribs 100 will have a height roughly equal to a height of the cap 82. A plurality of internal slots 108 are defined between each set of adjacent internal ribs 100. The internal ribs 100, in a preferred form of the invention, will have a width that tapers inwardly from proximate the bottom wall 102 to a top 104 of the internal ribs 100 so that the width of the internal ribs decrease from a bottom 106 of a rib to the top 104 of the rib. Also, it is preferable that the top of the internal ribs 100 have a generally arcuate profile to act as a lead-in during insertion of the antiseptic cap assembly 80 into the housing 60. In a preferred form of the invention, the internal ribs 100 will terminate short of a top 113 of the housing sidewall 62 to define an annular gap 111 between the top of the rib 104 and the top 113. Also, extending radially inwardly from the internal surface 63 of the cap 82 is a detent 109 positioned proximate a top portion 113 of the side wall 62.

Figure 11:
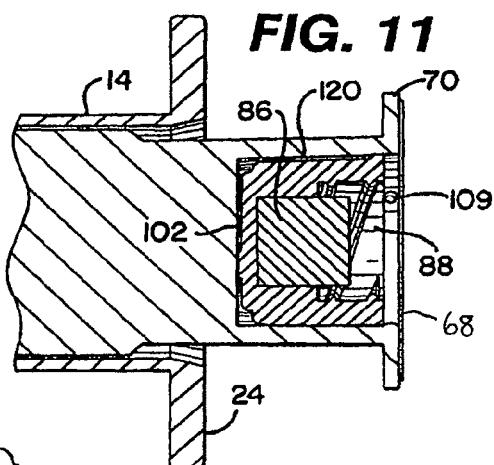
FIG. 11 shows an exploded view of a detail of FIG. 9 of another embodiment of the antiseptic cap equipped plunger and syringe barrel assembly.

The antiseptic cap 82 has a plurality of circumferentially spaced and axially extending ribs 120 extending along an external surface 121 of the cap 83 of cap 82 (external ribs 120). In one preferred form of the invention external ribs 120 extend between annular flange 123 at a proximal end 124 of the cap 82 to a position proximate a distal end 126 of the cap 82. The external ribs 120 are dimensioned for engaging a portion of the interior wall surface 63 of the housing 62 to prevent relative rotation of the cap assembly 80 and the plunger assembly 12. Spacing between the external ribs define a plurality of external slots 122 between each adjacent pair of external ribs 120. When the cap 82 is positioned within the chamber 64 (FIGS. 9 and 11) each of the external ribs 120 are positioned within an internal slot 108 and each of the internal ribs 100 are positioned within an external slot 122 to lock together these parts to assure that the cap rotates in the same direction as the plunger rod assembly 12. FIGS. 6 and 11 also show that when the cap 82 is positioned within the housing 60, the detent 109 contacts the annular flange 123 to hold the cap assembly 80 in the plunger housing chamber 64 to prevent or resist inadvertent dropping of the cap assembly 80 from the housing chamber 64 prior to docking of the cap assembly 80 with the access site 38.

Figure 12:
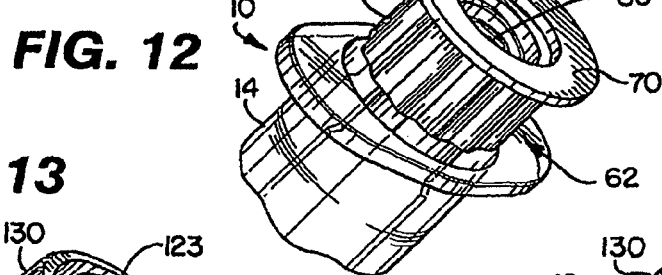
FIGS. 12-14 show various embodiments of grips of the antiseptic cap equipped plunger assembly.
Figure 13:
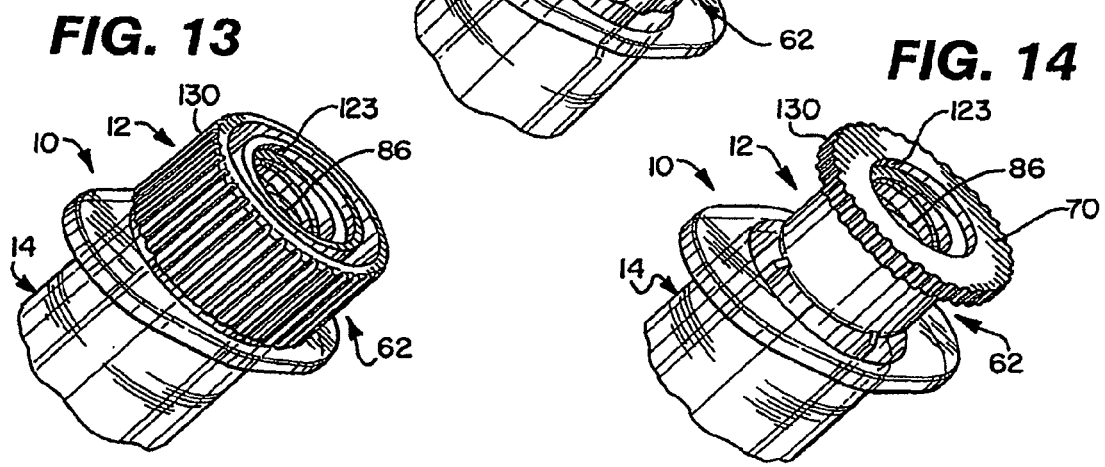
Figure 14:
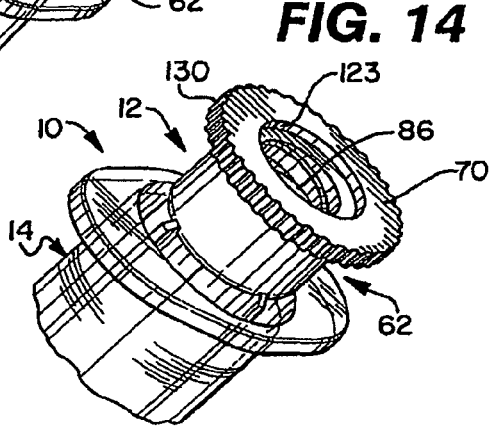
Figure 15:
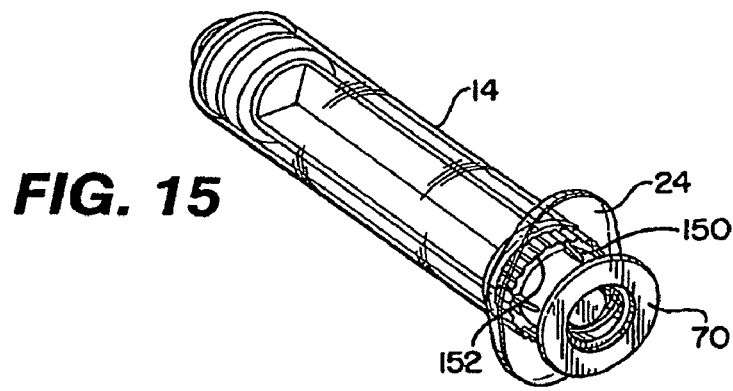
FIGS. 15-17 show various views of one embodiment antiseptic cap equipped plunger and syringe barrel assembly with a barrel lock to resist rotation of the plunger assembly with respect to the syringe barrel.
Figure 16:
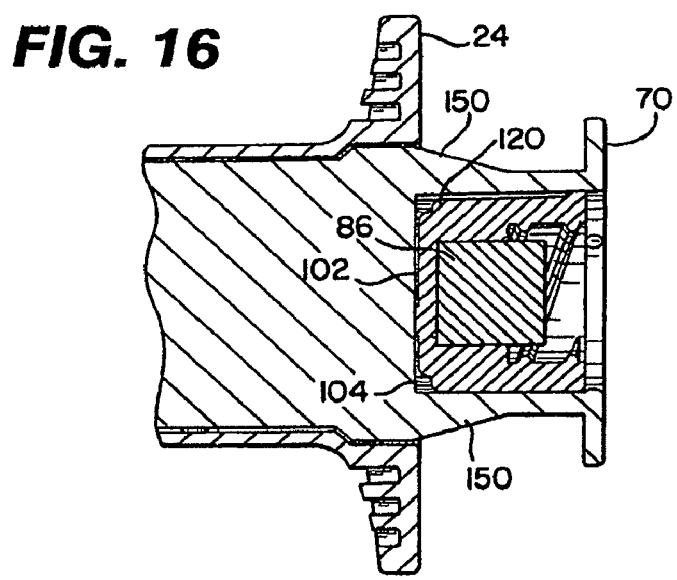
Figure 17:
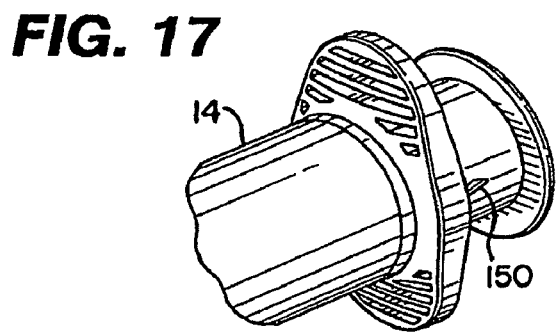

FIGS. 12-14 show several embodiments of gripping surfaces on the housing 60 (with lid stock 68 removed) to facilitate use of the assembly 10 or the plunger assembly 12. FIG. 12 shows axially extending and circumferentially spaced protuberances 130 on an outer surface of the wall 62. The protuberances 130 can have numerous different cross-sectional shapes including circular, polygonal, oval and irregular and, in a preferred form of the invention, extend from the flange 70 to a bottom of the housing.

FIG. 13 shows a housing 60 that has no flange 70 and has protuberances 130 on the wall 62 extending substantially the entire height of the housing 60. FIG. 14 shows a housing 60 where the outer surface of the wall 62 is relatively smooth but has a series of circumferentially spaced and axially extending protuberances 130 on a circumferential edge of the flange 70.

As with the cap and plunger assembly rotational locking features or structures, the optional plunger assembly 12 and syringe barrel 14 locking feature or structure can be positioned alone on the plunger assembly 12, or alone on the syringe barrel 14 or have cooperating structures on both the plunger assembly 12 and the syringe barrel 14. It is also contemplated that a separate mechanism, device or member could be used to lock the two parts together to achieve this purpose.

FIGS. 15-18 show various embodiments for the optional feature of locking the plunger assembly 12 from rotational motion with respect to the syringe barrel 14. In one embodiment shown in FIGS. 15-17 and 21 a wing 150 extending axially along an outside surface of the housing side wall 62 engages a tooth 152 positioned on an interior surface of the syringe barrel 14 at its proximal end 20. More preferably, the plunger assembly 12 will have more than one wing 150 with each wing being circumferentially spaced from the other. In an even more preferred form of the invention the plunger assembly will have four wings 150 spaced 90 degrees from one another. Also, in a more preferred form of the invention, the syringe barrel 14 will have a plurality of circumferentially spaced teeth 152. When the plunger assembly 12 is nearly fully inserted into the syringe barrel 14 each of the wings 150 will extend into a tooth 152 to prevent rotation of the plunger assembly 12 with respect to the syringe barrel 14.

Figure 18:
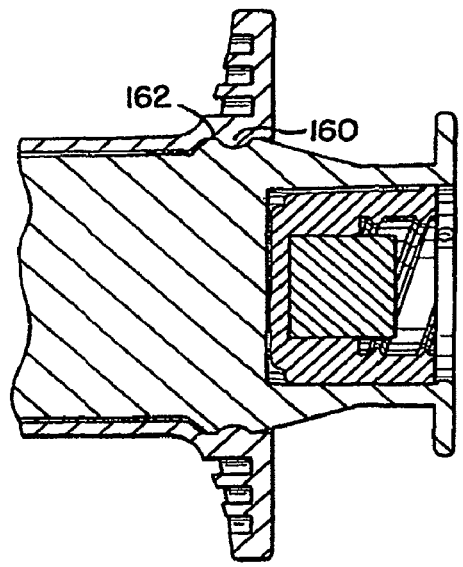
FIG. 18 shows another embodiment of a barrel lock to resist rotation of the plunger assembly with respect to the syringe barrel.

FIG. 18 shows another embodiment of a locking feature to prevent rotation of the plunger assembly 12 with respect to the syringe barrel 14 and also prevents relative translational motion of the parts. In this embodiment an annular protuberance 160 positioned on an interior surface of the syringe barrel at is proximal end 20 engages an annular detent 162 on an outside surface of the plunger rod.

Figure 19:
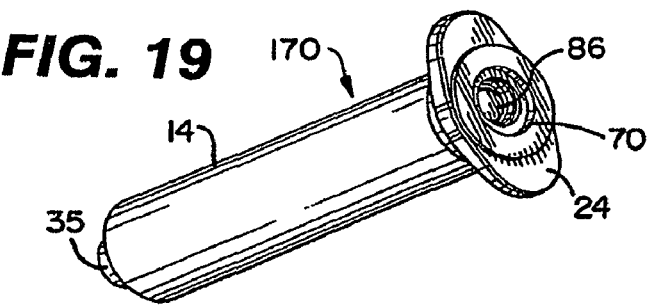
FIGS. 19-20 show various views of another embodiment antiseptic cap equipped plunger and anti-reflux syringe barrel assembly with a barrel lock to resist rotation of the plunger assembly with respect to the syringe barrel.
Figure 20:
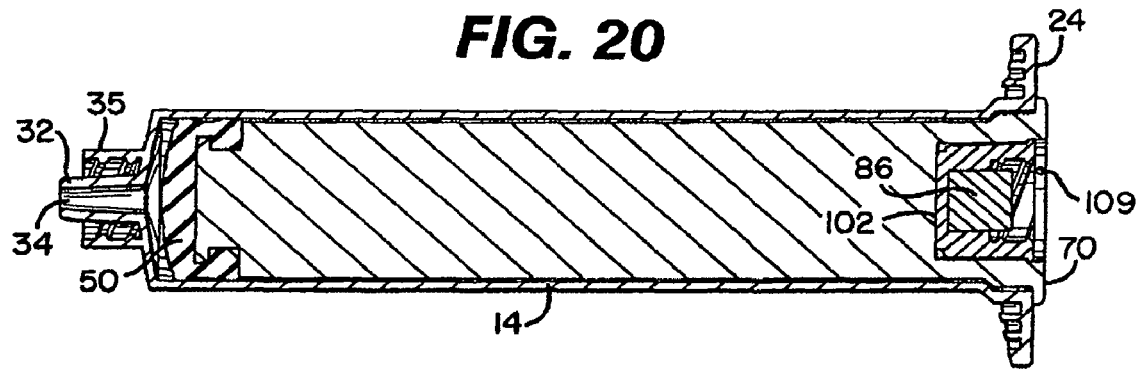
Figure 21:
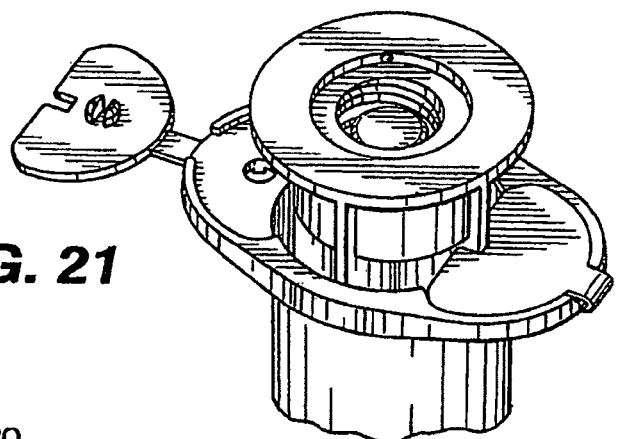
FIG. 21 shows a perspective view of another embodiment antiseptic cap equipped plunger and syringe barrel assembly with a barrel lock to resist rotation of the plunger assembly with respect to the syringe barrel.

FIGS. 19 and 20 show an antiseptic cap equipped plunger assembly 12 and non-refluxing syringe assembly 170. Non-refluxing syringes are well known in the art and there are numerous methodologies for reducing reflux while accessing the access site of a central venous catheter. In this embodiment the annular flange 70 of the plunger assembly 12 abuts the flange 24 of the syringe barrel prior to the piston 50 contacting an interior surface of the syringe distal end wall 30.

Figure 22A:
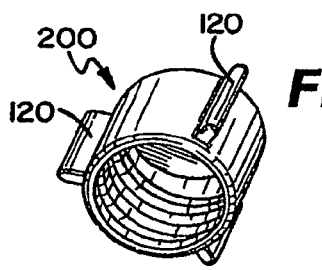
FIGS. 22a, b are respectively a perspective view of an antiseptic cap without a sponge and with a sponge.
Figure 22B:
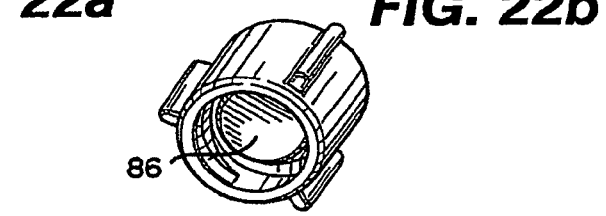
Figure 23:
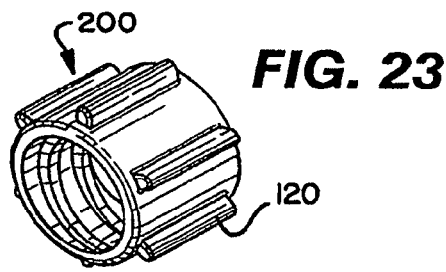
FIGS. 23 and 24 are different embodiments of the antiseptic cap with varying gripping features.
Figure 24:
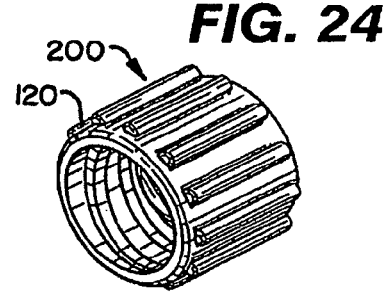

It is contemplated that the antiseptic cap assembly 80 of the present invention need not be coupled or combined with a plunger or a syringe barrel. FIGS. 22a, b show a stand-alone antiseptic cap assembly 200 having three circumferentially spaced ribs 120 for grasping by the hand of a user of the cap assembly. FIG. 22a shows the cap 82 without an absorbent material 86 and FIG. 22b shows the cap with an absorbent material. The cap 200 can be used for the same purposes of the cap assembly 80 described above but will be used by hand. All other features of the cap 200 are essentially the same as described above with the exception that the cap 200 does not have to be dimensioned to fit within a chamber carried by a syringe plunger. FIGS. 23 and 24 show varying frequency of ribs 120 and varying shapes and sizes.

Figure 25:
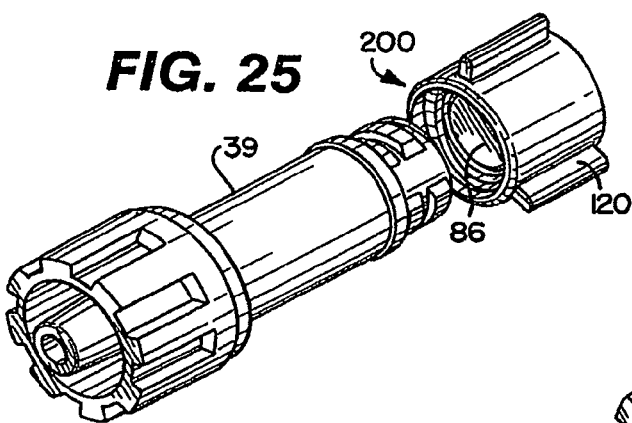
FIG. 25 is a perspective view of the antiseptic cap of FIG. 22b prior to docking with a valve.
Figure 26:
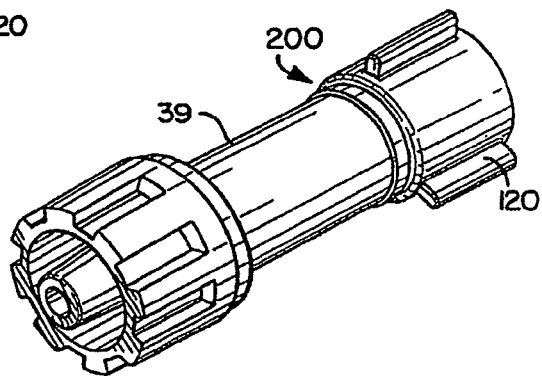
FIG. 26 is a perspective view of the antiseptic cap of FIG. 22b docked with a valve.
Figure 27:
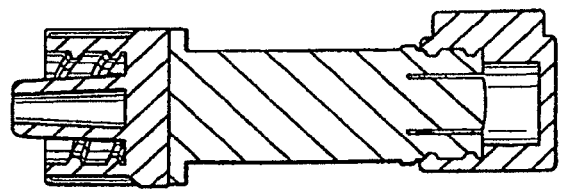
FIG. 27 is a side view in cutaway of the antiseptic cap and valve assembly shown in FIG. 26.

FIG. 25 shows the cap 200 proximate the access site 38 and FIGS. 26 and 27 show the cap 200 docked to the access site 38.

Figure 28:
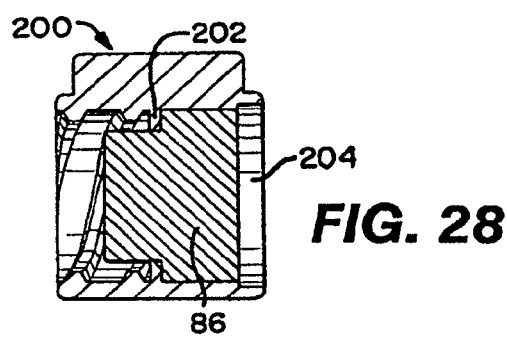
FIGS. 28-30 are side views in cutaway of two different embodiments of the antiseptic cap.

A suitable absorbent material 86 includes medical grade materials capable of storing and releasing an antiseptic liquid, or liquid having other medical purposes, and includes materials such as sponges, rupturable capsules and other materials or devices capable of serving this purpose. Suitable sponges can include any sponge suitable for use for medical purposes and can be naturally occurring or synthetic. The sponges can be die cut into suitable shapes or can be molded into the desired shape. It is desirable that the sponge 86 be attached to the antiseptic cap 82 to prevent the sponge 86 from inadvertently falling out of the cap 82. FIG. 28 shows the sponge 86 is captured between an annular wall 202 and a disc 204 attached to the cap 82 by any suitable method such as ultrasonic or vibrational welding or other techniques well known in the art.

Figure 29:
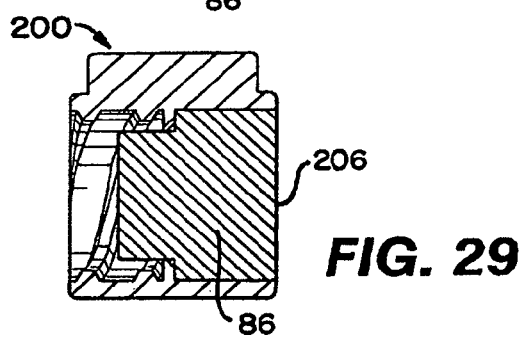
Figure 30:
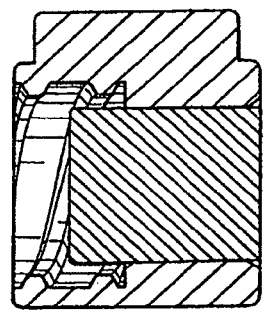

FIGS. 29 and 30 show a variation on the cap assembly 200 of FIG. 28. In this embodiment, the sponge is retained in the cap 82 with a plastic sheet 206 heat welded to the cap. In one preferred form of the invention the sponge is attached by an adhesive or by other method to form an assembly which is then attached to the cap.

Figure 31A:
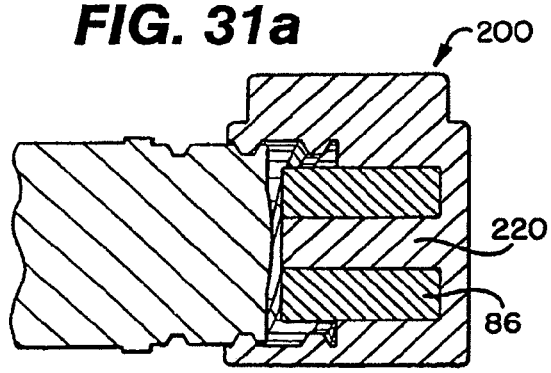
FIGS. 31 a,b are, respectively, side views in cutaway showing an antiseptic cap with a centrally disposed actuation post mounted on a valve with the valve in the unactivated and activated positions.
Figure 31B:
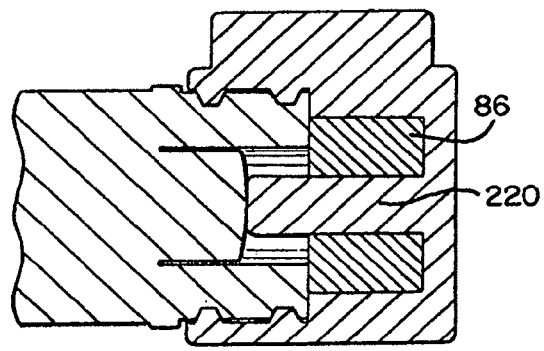

FIGS. 31 a, b show the cap 200 having a coaxially disposed and axially extending actuating post 220 circumferentially surrounded by a sponge 86 having a centrally positioned hole to fit over the post 220. FIG. 31a shows the cap 200 in initial engagement with the access site 38 and FIG. 31b shows the cap threaded onto the access site 38 and the actuating post opens the valve 39 and antiseptic fluid is allowed to flow into the valve.

Figure 32:
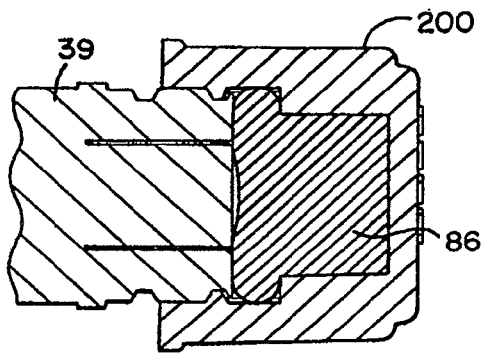
FIGS. 32 and 33 are side views in cutaway showing two different embodiments of an antiseptic cap having a molded sponge.
Figure 33:
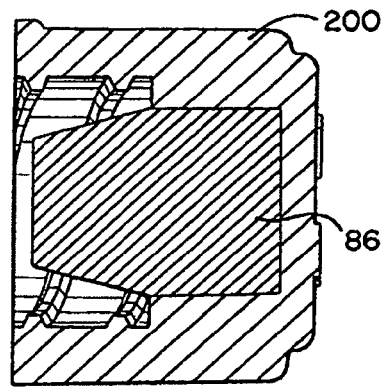
Figure 34:
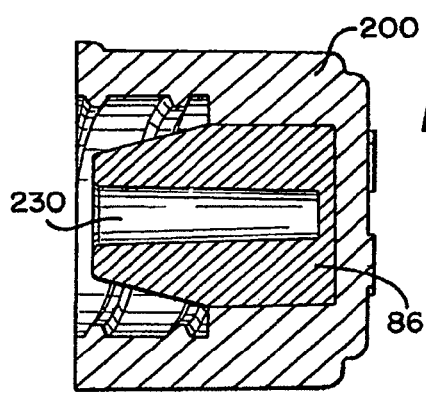
FIG. 34 is a side view in cutaway showing another embodiment of an antiseptic cap having a molded sponge docked to a valve.
Figure 35:
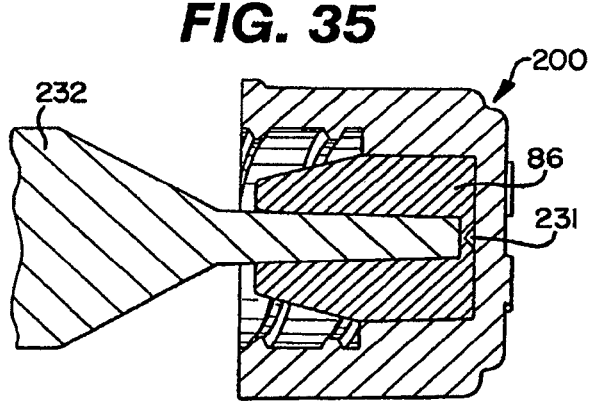
FIG. 35 is a side view in cutaway showing a step of attaching a molded sponge to an antiseptic cap.
Figure 36:
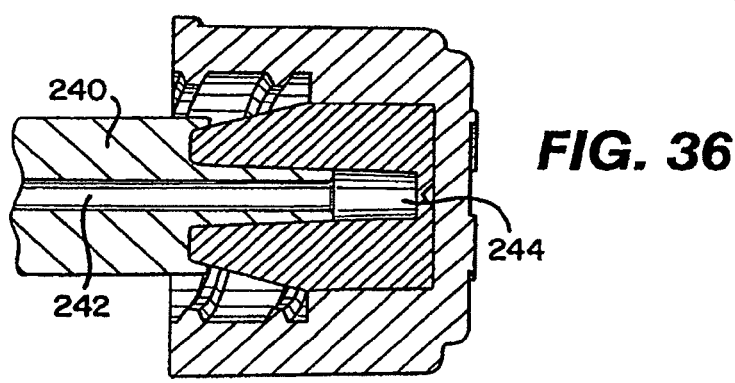
FIG. 36 is a side view in cutaway showing a step of delivering an antiseptic compound to a molded sponge positioned within a cap.

FIGS. 32-34 show varying shaped sponges that, in one preferred form of the invention, were molded into various desirable shapes. The sponge of FIG. 34 has a central opening 230 to facilitate attaching the sponge to the cap and to filling the sponge with antiseptic, anticoagulant or other suitable fluids set forth above. FIG. 35 shows the cap having a centrally disposed energy director 231, an ultrasonic welder 232 being brought into cooperative engagement with the sponge on a side of the sponge opposite the energy director 231. By applying ultrasonic energy the energy director 231 melts and attaches the sponge to the cap. FIG. 36 shows a filling device 240, having a lumen 242 and a dispensing head 244 in fluid communication with a source of antiseptic, anticoagulant or the like for dispensing a metered amount of such fluid into the interior portion of the sponge.

Figure 37:
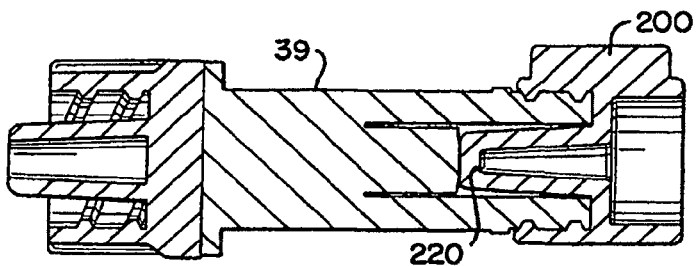
FIG. 37 shows a side view in cutaway of an antiseptic cap docking to a valve with the antiseptic cap having an antiseptic coating.

FIG. 37 shows an alternative embodiment of the antiseptic cap 200 where the sponge is replaced by an antiseptic coating on the actuating post 220.

Figure 38:
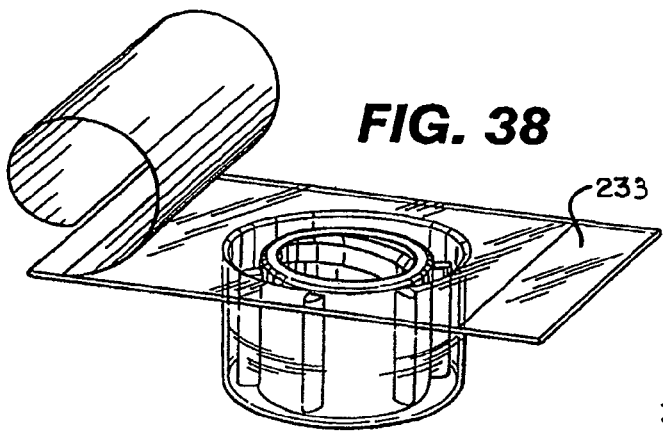
FIG. 38 shows a perspective view of an antiseptic cap in a blister package.

FIG. 38 shows the antiseptic cap 200 positioned in a blister pack 233 prior to sealing the blister pack.

Figure 39:
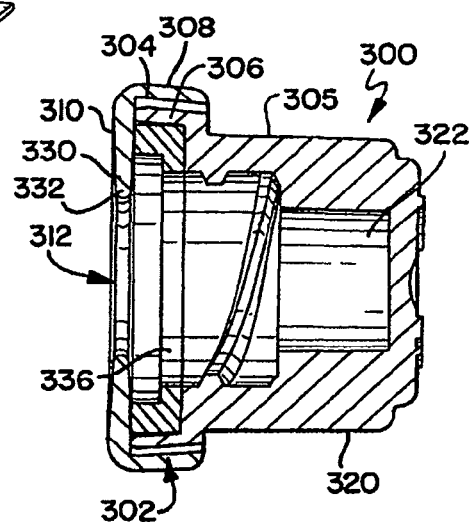
FIG. 39 is a side cross-sectional view of an antiseptic cap with a thread cover.

FIG. 39 shows an antiseptic cap 300 with a thread cover 302. The thread cover 302 can be part of any of the antiseptic caps discussed herein. The thread cover 302 is made of a deformable material capable of flexing upon application of moderate force applied by hand. In one preferred form of the invention the thread cover 302 is made from a polymeric containing material and more preferably a polymeric material having a modulus of elasticity of less than 20,000 psi. In another preferred form of the invention the polymeric material will be an elastomer or plastomer or like material. The thread cover 302 enhances the connection between the antiseptic cap 300 and a device such as a valve or other access devices 38. The thread cover 302 provides a physical barrier to the ingress of pathogens, dust or other contaminants through the mating threads of the antiseptic cap 300 and the access device or valve to which it is docked. The thread cover 302 also serves to retain antiseptic fluids from the antiseptic cap 300 from leaking out through the threads. The thread cover can be made a part of the antiseptic cap 300 using techniques well known in the art such as overmolding, or by attaching as a separate part using welding techniques such as heat conductive welding, heat induction welding, vibrational welding, stretch or friction fit, or by using a suitable adhesive.

The thread cover 302 can provide a universal fit to most commercially available valves, connectors and access devices, or the thread cover 302 can be customized to dock with a particular access device.

FIG. 39 shows, as is described above, the antiseptic cap 300 has an annular wall 305 having a first end 306 and a second end 320 with the first end having a greater diametrical dimension than the second end. The annular wall defines a central chamber 322 having an open end 323. In one preferred form of the invention, the chamber 322 will have a sponge 86 positioned therein as shown in FIGS. 5 and 6 above, although it is not shown in FIG. 39. The thread cover 302 is shown attached by an optional bonding layer 304 to the first end 306 of the annular wall 305. The thread cover 302 has a first leg 308 and a second leg 310. The first leg 308 extends parallel to the annular wall 305 and the second leg 310 extends radially inwardly from the annular wall 305 in a direction transverse to the first leg 308 and across a portion of the open end 323 and defines a central opening 312, having a reduced diameter when compared to the open end 323, into the chamber 322. The second leg 310 terminates at a distal end 330 with a rounded outer surface 332.

Figure 40:
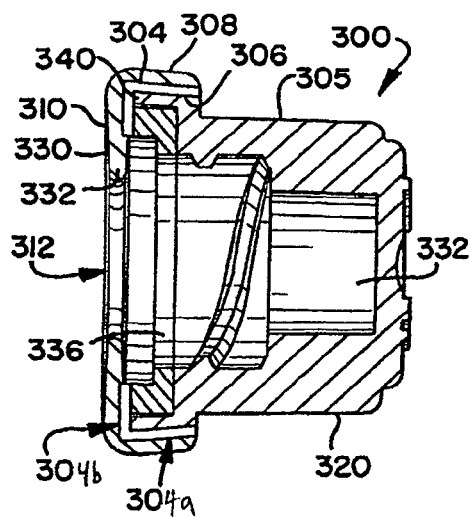
FIG. 40 is a side cross-sectional view of an antiseptic cap with a thread cover.

FIG. 40 shows an alternative embodiment of the antiseptic cap 300 having the thread cover 302 having both the first and second legs 308, 310 attached to the first end 306 of the annular wall 305 through bonding layers 304 a, b. A top surface 340 of the first end 306 is shown having the same thickness or diametrical dimension as the remainder of the first end but it is contemplated the top surface could have a radially extending flange 123 as shown in FIG. 5.

Figure 41:
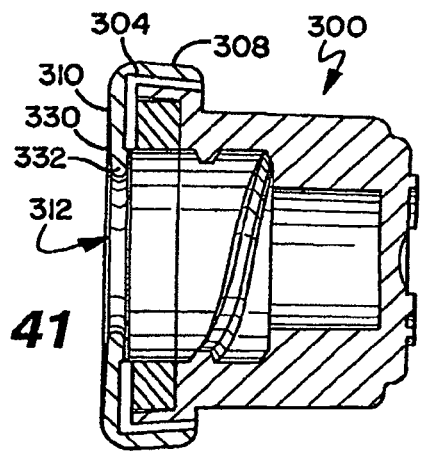
FIG. 41 is a side cross-sectional view of an antiseptic cap with a thread cover.

FIG. 41 shows an alternative embodiment of the antiseptic cap 300 that differs from the antiseptic cap shown in FIGS. 39 and 40 by not including a counterbore 336 shown in these figures. The counterbore 336 provides a chamber of reduced diameter and, therefore, will form a tighter fit with access devices with a more narrow outer diameter when compared to the cap shown in FIG. 41 which does not include the counterbore. This is just one example of the modifications that can be made to the geometry of the antiseptic cap to enhance the connection between the cap and an access site.

Figure 42A:
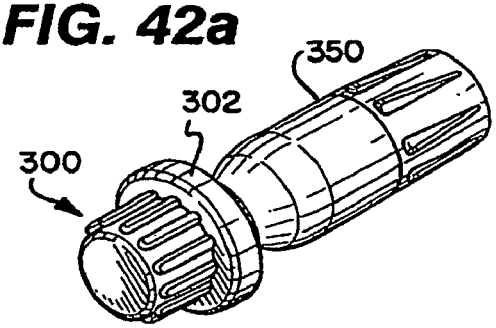
FIGS. 42a,b are perspective front and back views of an antiseptic cap with a thread cover connected to a Cardinal SMART SITE access site.
Figure 42B:
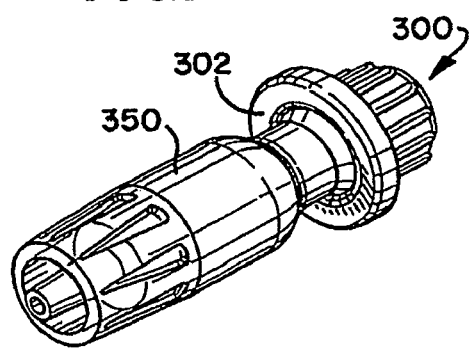
Figure 43A:
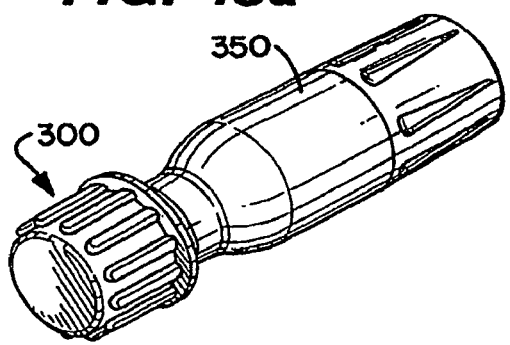
FIGS. 43 a,b are perspective front and back views of an antiseptic cap without a thread cover connected to a Cardinal SMART SITE access site.
Figure 43B:
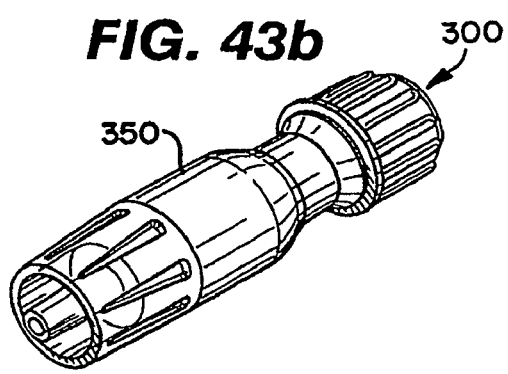

FIGS. 42a,b show front and back views of the antiseptic cap 300 with the thread cover 302 connected to a Cardinal SMART SITE access site 350. FIGS. 43 a,b are perspective front and back views of the antiseptic cap without the thread cover 302 connected to the Cardinal SMART SITE access site.

Figure 44A:
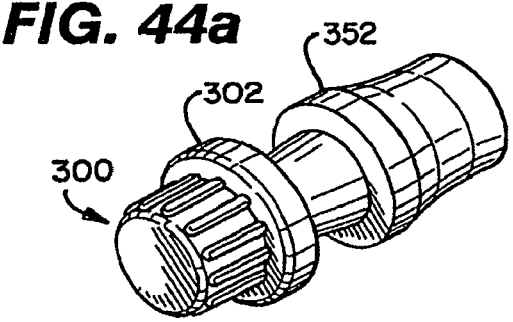
FIGS. 44 a,b are perspective front and back views of an antiseptic cap with a thread cover connected to a Hospira (ICU) C1000 Clave access device.
Figure 44B:
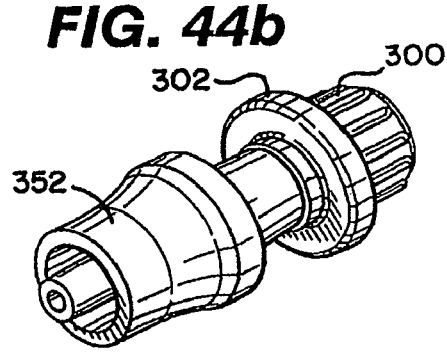
Figure 45A:
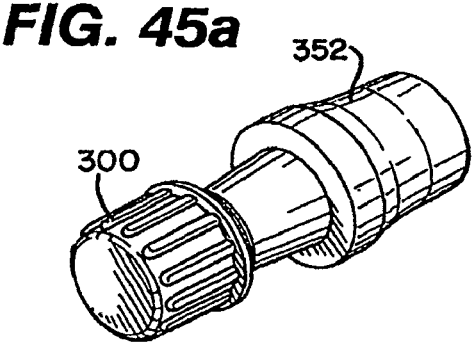
FIGS. 45 a,b are perspective front and back views of an antiseptic cap without a thread cover connected to a Hospira (ICU) C1000 Clave access device.
Figure 45B:
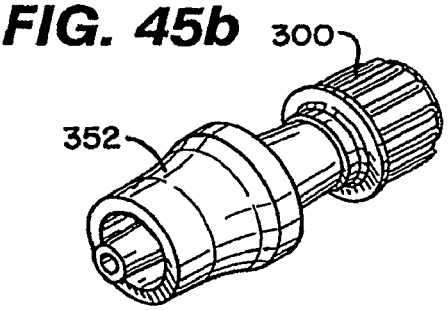

FIGS. 44a,b are perspective front and back views of the antiseptic cap 300 with the thread cover 302 connected to a Hospira (ICU) C1000 Clave access device 352. FIGS. 45a,b are perspective front and back views of the antiseptic cap, without a thread cover 302, connected to the Hospira (ICU) C1000 Clave access device.

Figure 46A:
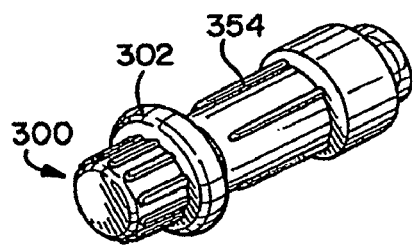
FIGS. 46 a,b are perspective front and back views of an antiseptic cap with a thread cover connected to a B. Braun ULTRASITE access device.
Figure 46B:
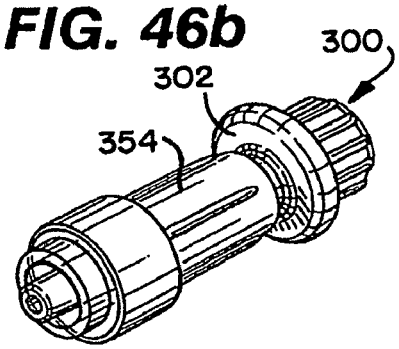
Figure 47A:
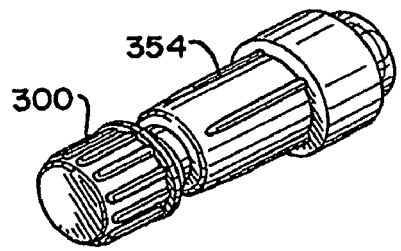
FIGS. 47 a,b are perspective front and back views of an antiseptic cap without a thread cover connected to a B. Braun ULTRASITE access device.
Figure 47B:
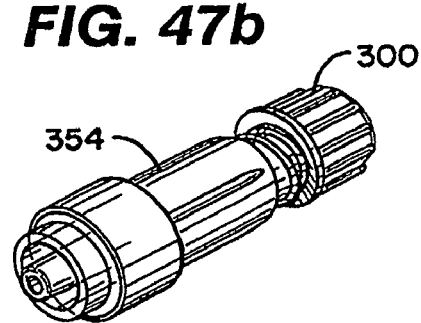

FIGS. 46a,b are perspective front and back views of the antiseptic cap 300 with the thread cover 302 connected to a B. Braun ULTRASITE access device 354. FIGS. 47a,b are perspective front and back views of the antiseptic cap without the thread cover 302 connected to the B. Braun ULTRASITE access device.

Figure 48A:
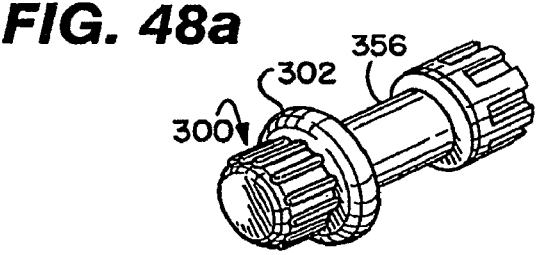
FIGS. 48 a,b are perspective front and back views of an antiseptic cap with a thread cover connected to a Rymed INVISION PLUS access device.
Figure 48B:
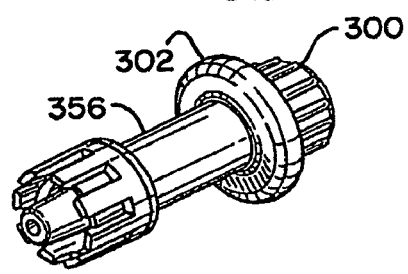
Figure 49A:
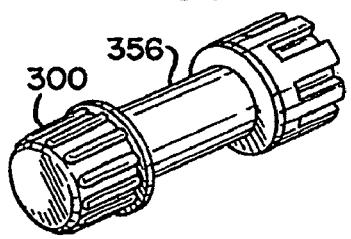
FIGS. 49 a,b are perspective front and back views of an antiseptic cap without a thread cover connected to a Rymed INVISION PLUS access device.
Figure 49B:
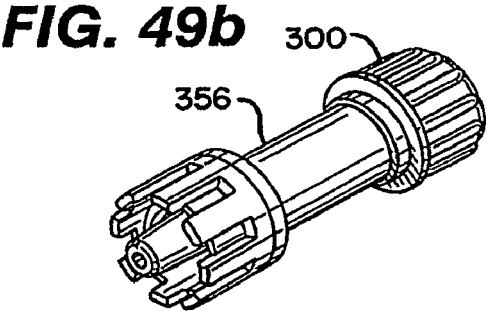

FIGS. 48a,b are perspective front and back views of the antiseptic cap with the thread cover 302 connected to a Rymed INVISION PLUS access device; 356. FIGS. 49a,b are perspective front and back views of the antiseptic cap without the thread cover 302 connected to a Rymed INVISION PLUS access device.

Figure 50:
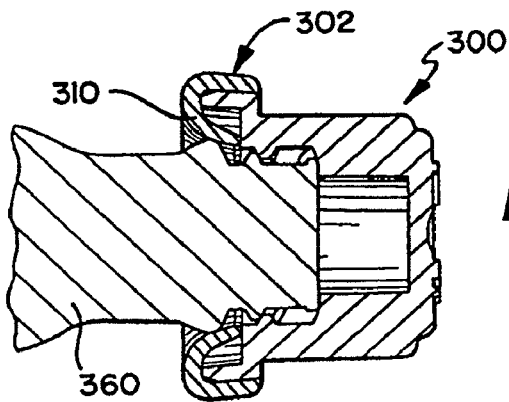
FIG. 50 is a side cross-sectional view of an antiseptic cap with a thread cover connected to a Cardinal SMARTSITE PLUS access device.
Figure 51:
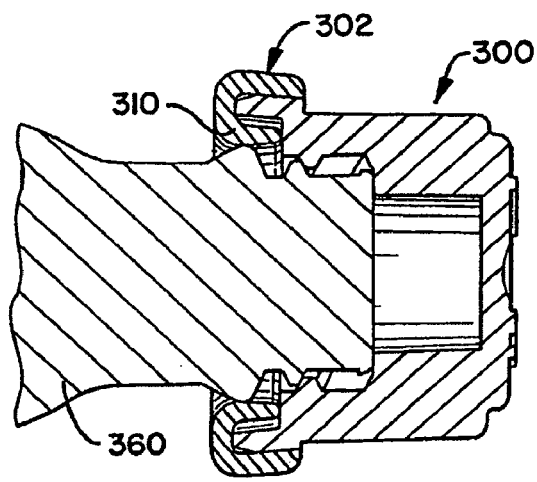
FIG. 51 is a side cross-sectional view of an antiseptic cap with a thread cover connected to a Cardinal SMARTSITE PLUS access device and the thread cover having a reduced diameter when compared to the thread cover shown in FIG. 50.
Figure 52:
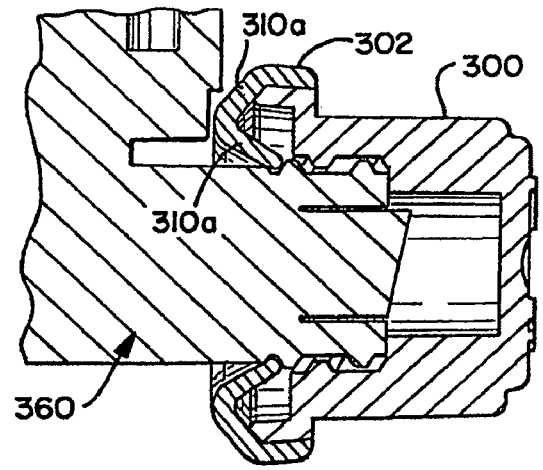
FIG. 52 is a side cross-sectional view of an antiseptic cap with a thread cover connected to a Hospira (ICU) C1000 Clave access device having a thread cover with an alternative profile.

FIGS. 50-52 show various embodiments of the thread cover 302. FIG. 50 differs from FIG. 51 in that the second leg 310 extends farther across the opening of the chamber in FIG. 51 than shown in FIG. 50. FIG. 52 shows another embodiment of the thread cover 302 having a segmented second leg 310a,b. This embodiment may be desirable to provide a more effective seal for certain access devices.

Figure 53:
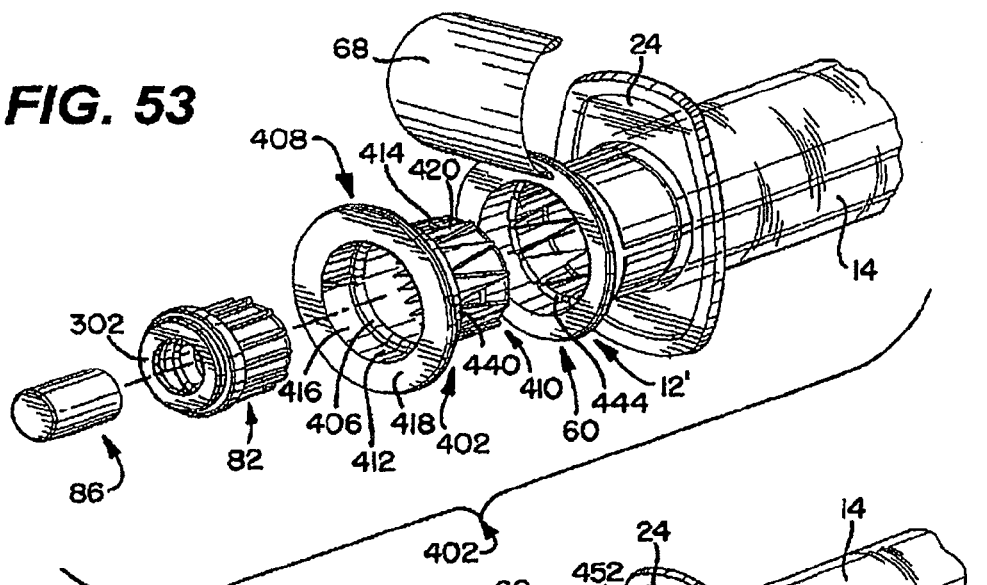
FIG. 53 is an assembly view of an antiseptic cap and cup holder equipped plunger and syringe barrel system.
Figure 54:
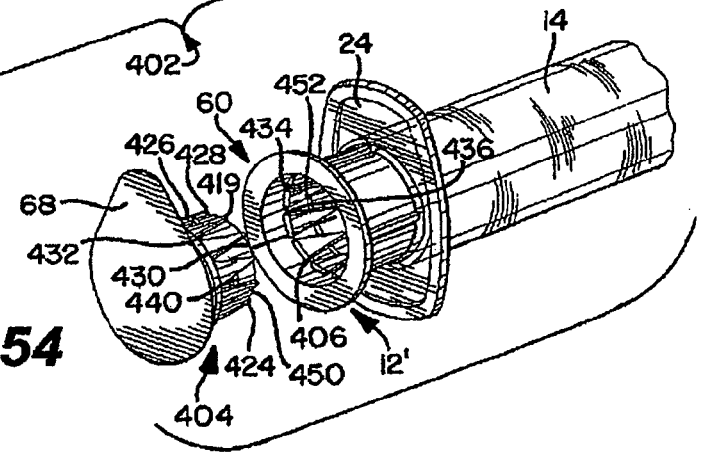
FIG. 54 is an assembly view of a cup-holder-antiseptic cap assembly adjacent a plunger and syringe barrel system.
Figure 55:
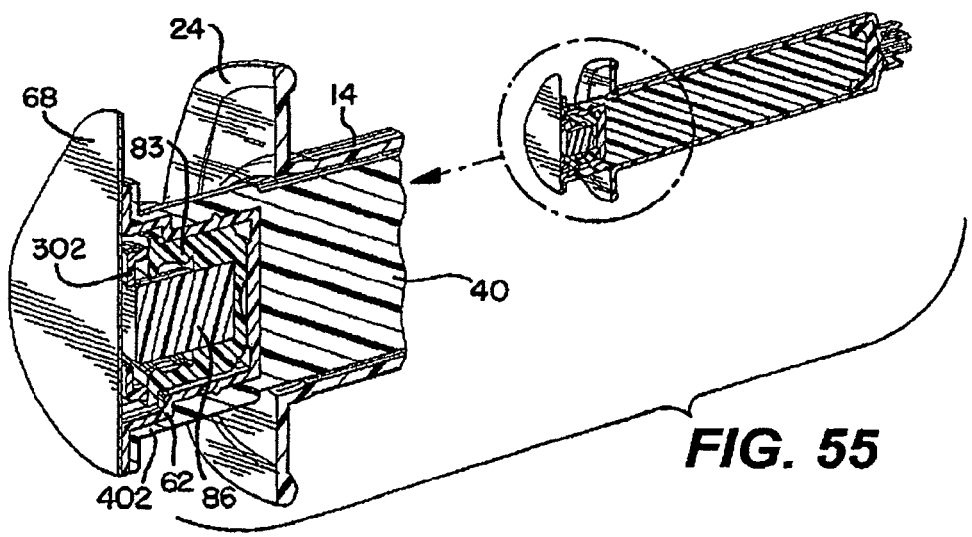
FIG. 55 is a side view in cross-section of an antiseptic cap and cup holder equipped plunger and syringe barrel assembly.

FIG. 53 shows an exploded view of an alternative embodiment 400 of the syringe barrel assemblies 10, discussed above, incorporating a cap holder 402 into the system of parts. Thus, the alternative assembly and system 400 has an antiseptic cap and cap holder equipped plunger assembly 12', a syringe barrel 14, an antiseptic cap 82 (shown with an optional thread cover 302), an absorbent material 86, and peelable lid stock 68. FIG. 54 shows an exploded view of an antiseptic cap holder assembly 404 including the cap holder 402 with the antiseptic cap assembly 80 positioned within a chamber 406 of the cap holder 402. This embodiment 400 allows for the separate manufacture, assembly, and sterilization of the assembly 400 from the plunger assembly and the syringe barrel.

The cap holder 402 has a proximal and distal ends 408, 410, and an inner wall surface 412 and an outer wall surface 414, an opening 416 into the chamber 406, and a radially outwardly extending flange 418 circumjacent the opening 416 and extending from the proximal end 408 of the cap holder 402. The cap holder 402 will also have an optional bottom wall 419.

In a preferred form of the invention, the cap holder 402 or the antiseptic cap 82 will have a structure, element or the like that prevents the relative rotation of the cap holder 402 and the antiseptic cap 82 until the antiseptic cap assembly 80 is securely docked to the access device 38. Also, in a preferred form of the invention the cap holder 402 or the plunger assembly 12' will have a structure, element or the like for preventing the relative rotation of the cap holder 402 and the plunger assembly 12' until the antiseptic cap assembly 80 is securely docked to the access device 38. Any of the anti-rotation devices discussed above to stop the rotation of the antiseptic cap assembly 80 with the plunger assembly 12 would be suitable for, these purposes. Also, it is contemplated the devices discussed above in reference to FIGS. 15-21 to prevent the relative rotation of the plunger assembly 12 and the syringe barrel 14 could be incorporated into this embodiment 400.

FIG. 53 shows the inner wall surface 412 of the cap holder 402 carries the internal ribs 100 and the internal slots 108 that interact with the external ribs and external slots 120, 122 of the cap 82 as is described above with respect to FIG. 5. These structures prevent or resist the relative rotation of the cap holder 402 with respect to the antiseptic cap assembly 80. The term "ribs" referred to herein are structures that are raised or extend outward from a surface. The term "slots" refer to structures that extend below a surface or is defined between two ribs and is at a lower level than the ribs.

FIG. 53 also shows an interlocking structure for preventing the relative rotation of the cap holder 402, or the cap holder assembly 404, with respect to the plunger assembly 12'. The outer wall surface 414 has a plurality of circumferentially spaced and axially extending ribs 420 defining slots 424 between each pair of adjacent ribs. In a preferred form of the invention, the ribs 420 are generally triangular in shape having a base portion 426 and an apex portion 428. The slots 424 are oppositely-oriented triangularly shaped areas having slot base portions 430 extending between two adjacent rib apex portions 428 and slot apex portions 432 separating adjacent rib base portions 426. On the internal wall surface 63 of the plunger chamber 64 are similarly shaped plunger ribs 434 and plunger slots 436. The ribs 420 are dimensioned to fit within the plunger slots 436 and the slots 424 are dimensioned to fit over and receive the plunger ribs 434. Thus, when the cap holder 402 or the cap holder assembly 404 is inserted in the plunger chamber 64 the cap holder ribs 420 are interdigitated with the plunger ribs 434 to prevent or resist the relative rotation of the cap holder 402, or cap holder assembly 404, with respect to the plunger assembly 12'.

In yet another preferred form of the invention, the cap holder 402, the cap holder assembly 404 or the plunger assembly 12' will have a structure, element or the like that resists the relative axial movement of these parts when the cap holder 402 or the cap holder assembly 404 is positioned fully within the plunger assembly 12'. In one preferred form of the invention the cap holder 402 has an annular protuberance 440 that is dimensioned to fit within an annular groove 442 on the inner wall surface 414 of the cap holder and preferably extends in line with the base portions of the plunger ribs 434. A second locking structure is provided having a plurality of teeth 450 which extend axially outward from the outer wall surface 414 of the cap holder and are positioned in slots 424. In a preferred form of the invention the teeth extend axially outwardly to a height beyond the height of the ribs 434. The teeth 450 can be positioned in one or more of the slots or in each of the slots 424 or in alternating slots or, as is shown, circumferentially spaced 90° from one another. The teeth 450 preferably are positioned at an intermediate portion, between the base and the apex, of a slot 424. The teeth 450 are dimensioned to fit within a segmented annular groove 452 that extends circumferentially about the inner surface 412 crossing through the plunger ribs 434 at an intermediate portion, between the base and the apex, of the plunger ribs 434.

Figure 56A:
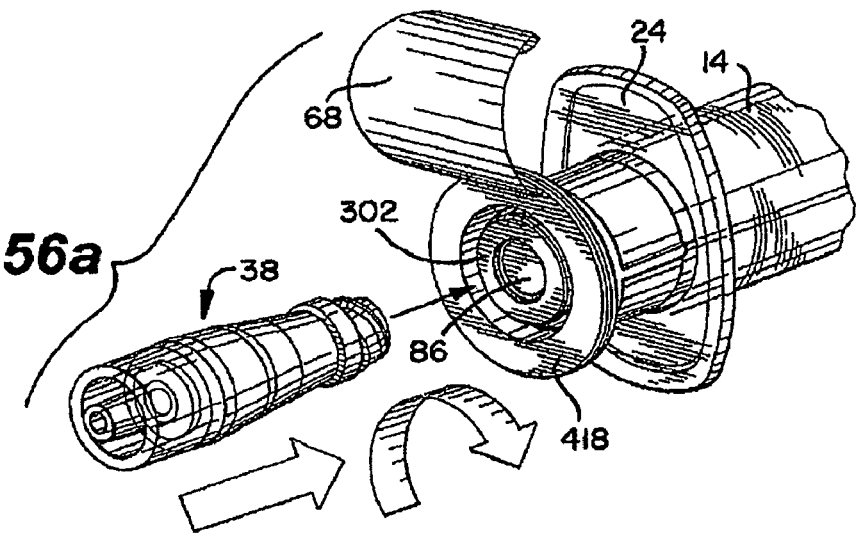
FIG. 56a is a perspective view of a medical access device adjacent an antiseptic cap equipped plunger and syringe barrel assembly with a lid stock peeled back in preparation for docking.
Figure 56B:
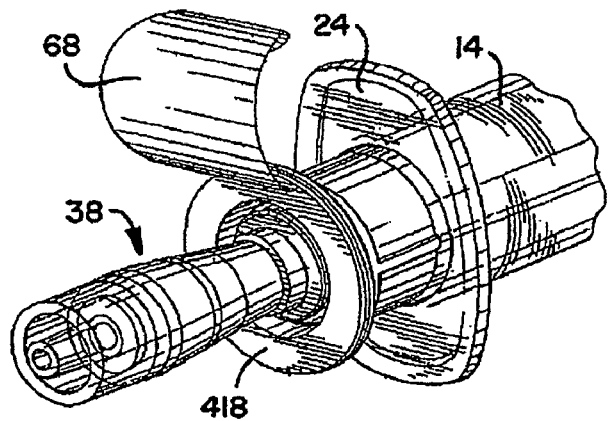
FIG. 56b is a perspective view of a medical access device docked to an antiseptic cap equipped plunger and syringe barrel assembly.
Figure 56C:
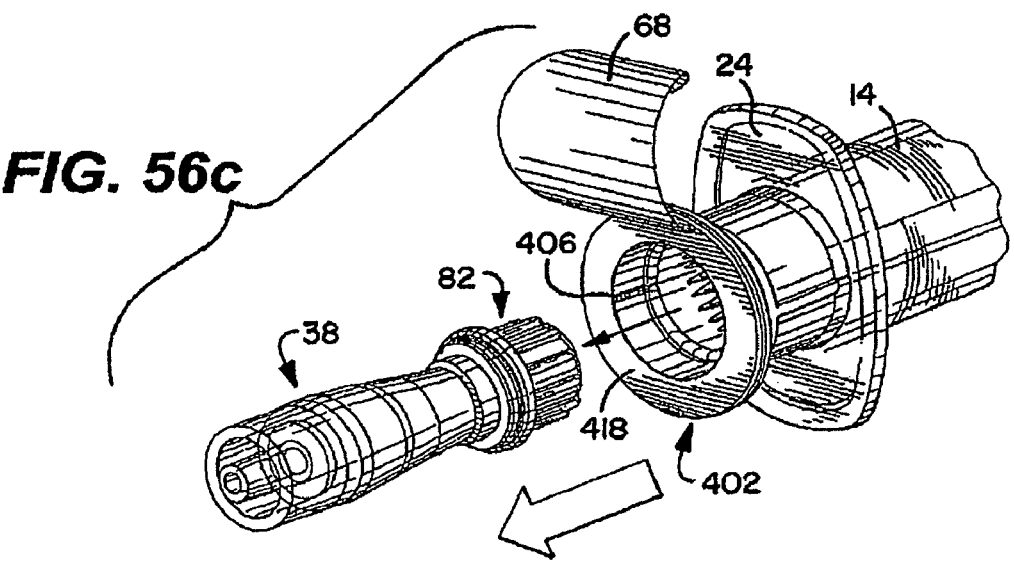
FIG. 56c is a perspective view of a medical access device docked to an antiseptic cap adjacent a plunger and syringe barrel assembly.
Figure 57:
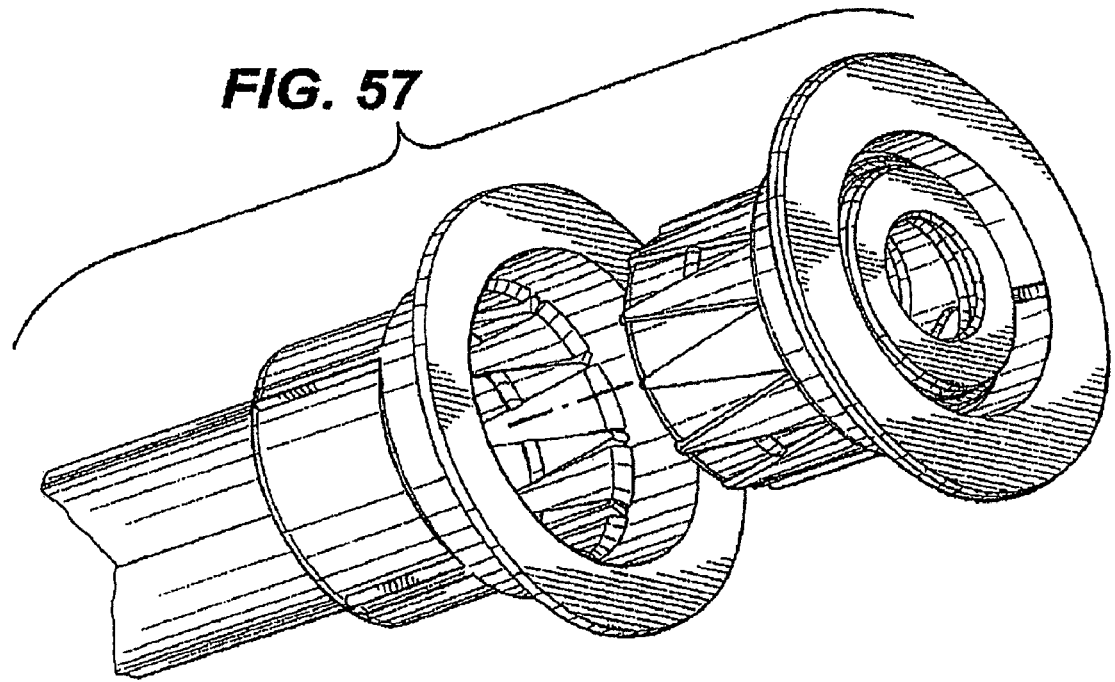
FIG. 57 is an enlarged view of a cup holder and antiseptic cap assembly adjacent an open and empty chamber of a syringe plunger.
Figure 58:
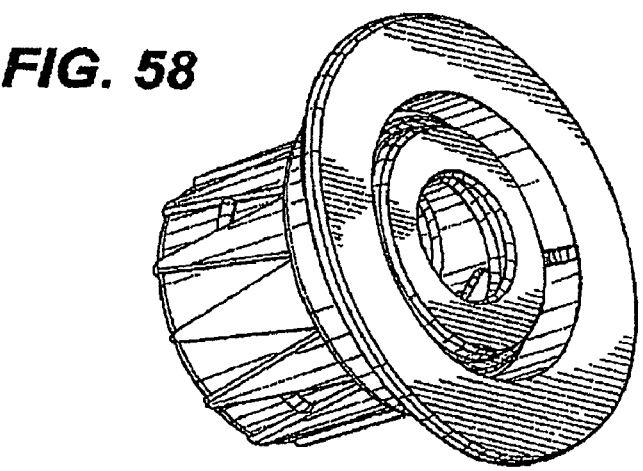
FIG. 58 is an enlarged view of a cup holder and antiseptic cap assembly positioned within a chamber of a syringe plunger.

FIGS. 56a,b,c respectively show the assembly 400 in a ready-for-use position, docked position, and used position. The assembly 400 is used in essentially the same fashion as described above with respect to FIGS. 3 and 4 except that when the assembly 400 is in the used position the cap holder 402 remains in the plunger assembly 12'.

The syringe barrel and plunger can be fabricated from any material suitable for its purpose and includes glass and polymeric material. Suitable polymeric materials include, but are not limited to, homopolymers, copolymers and terpolymers formed from monomers such as olefins, cyclic olefins, amides, esters, and ethers. The polymeric material may be a blend of more than one polymeric material and can be a monolayer structure or a multilayer structure. In one preferred form of the invention the syringe barrel and the plunger are injection molded from a polypropylene material.

Figure 59:
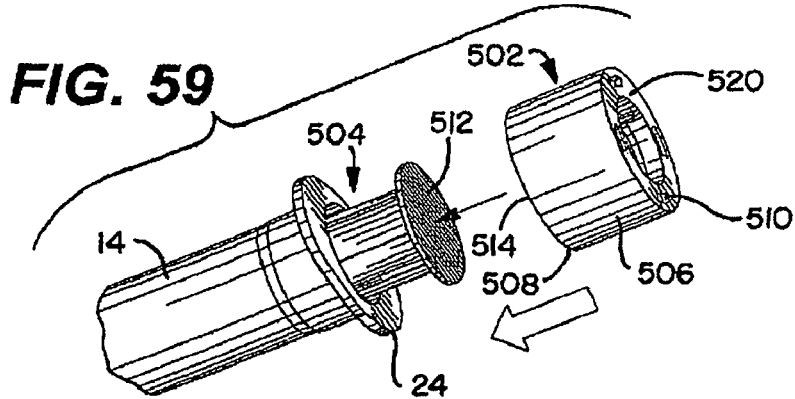
FIG. 59 is a perspective view of an alternative embodiment of an antiseptic cap assembly adjacent a syringe plunger and barrel assembly.
Figure 60:
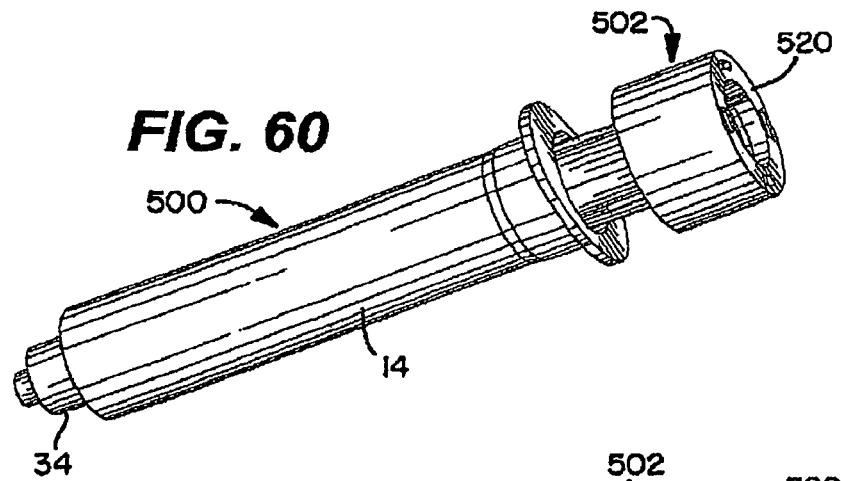
FIG. 60 is a perspective view of an alternative embodiment of an antiseptic cap assembly docked to a syringe plunger and barrel assembly.
Figure 61:
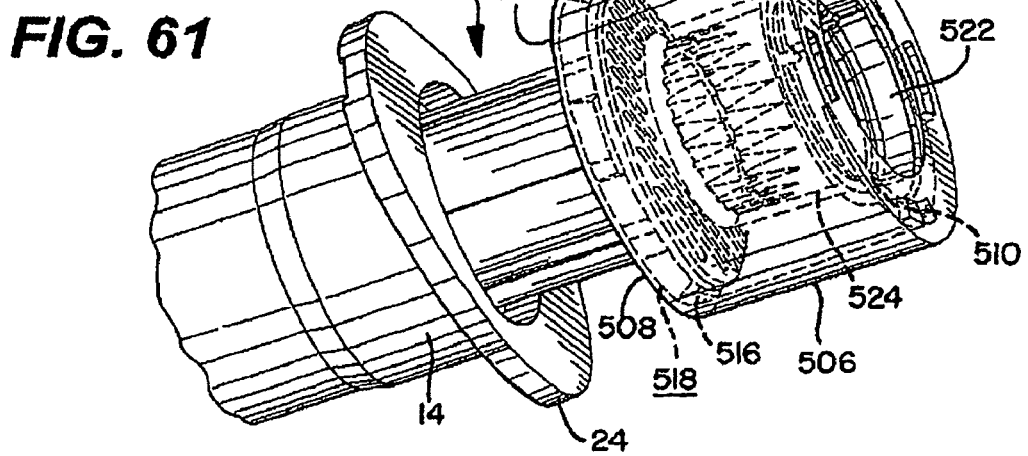
FIG. 61 is a perspective view of an alternative embodiment of an antiseptic cap assembly docked to a syringe plunger and barrel assembly with an outer wall being transparent to reveal interior portions of the assembly.

FIGS. 59-61 show a third embodiment 500 of an antiseptic cap equipped syringe plunger and barrel assembly with the antiseptic cap assembly 80 and lid stock 68 removed for clarity. The third embodiment 500 provides for retrofitting an antiseptic cap assembly 502 to a standard plunger 504. The antiseptic cap 502 has a first generally cylindrical outer wall 506 having a proximal end 508 and a distal end 510. The proximal end 508 is removably or fixedly attached to a button 512 of the plunger 504. The proximal end has an opening 514 dimensioned to fit about the button 512 and has a member for attaching to the button. In one preferred form of the invention, the attaching member includes a plurality of circumferentially spaced, and axially inwardly directed tabs 516 extending from an inner wall surface 518 and the tabs engage a lower surface of the button 512 to attach the antiseptic cap assembly 502 to the plunger 504.

The distal end of the antiseptic cap 502 has a top annular flange 520 extending radially inwardly from the first cylindrical wall 506 and defines a generally circular opening 522. A second cylindrical wall 524 extends axially downwardly from the top annular flange 520 and is coaxially disposed within the first cylindrical wall 506. When the antiseptic cap 502 is attached to the plunger button 512 a bottom peripheral edge of the second cylindrical wall 524 will abut a top surface of the plunger button 512 thereby capturing, by oppositely directed axially forces, the plunger button 512 between the tabs 516 and the second cylindrical wall. It is contemplated, however, that a second set of tabs could be provided spaced axially away from the first set of tabs and the piston button 512 could be trapped between the two sets of tabs. Further, it is contemplated other attaching means could be used that are well know in the art and the attaching member shown is merely exemplary.

The second cylindrical wall 524 defines a chamber as is shown in greater detail in FIG. 5 above with the ribs and slots as described for engaging the antiseptic cap assembly 80 to prevent relative rotational movement and to resist relative axial movement of the parts when the antiseptic cap assembly 80 is fully inserted into the chamber. Further, it is contemplated adapting the plunger and syringe as described above to prevent or resist the relative rotational movement of the plunger with respect to the barrel.

The piston 50 can be formed from any suitable material including a polymeric material or a silicone material. The stopper can be selected from a material with a desired durometer so that reflux is reduced when the stopper engages an inner surface of the distal end wall of the syringe barrel.

Suitable locking and flush solutions include a lower alcohol selected from ethanol, propanol and butanol. The locking solution can be a single lower alcohol or a blend of lower alcohols.

Suitable locking solutions can also include a lower alcohol with an antimicrobial and or an anticoagulant. Suitable locking solutions can contain at least one lower alcohol in a range from 1% to 99% by volume and at least one other antimicrobial and/or anti-coagulant compound in a range from 1% to 99% by volume. The lower alcohol will usually be in aqueous solution, typically at 1% to 99% by volume, usually from 5% to 95% by volume. The at least one other antimicrobial is selected from the group consisting of taurolidine and triclosan, and the at least one anti-coagulant is selected from the group consisting of riboflavin, sodium citrate, ethylene diamine tetraacetic acid, and citric acid.

In one preferred form of the invention, the syringe assembly 10 will be pre-filled with one of the locking solutions and will be packaged by a manufacture and shipped to a health care provider. A cannula or needle will be attached to the distal end of the barrel and placed into fluid communication with the fluid access site of an indwelling central venous catheter. The flush solution will be injected into the catheter to clean or lock the catheter. Afterwards, the cap assembly 80 will be removed from the plunger 17 and the cap will be docked to the fluid access site of the catheter.

Citrate Salt Containing Antiseptic Solutions

In one form, the antiseptic is a solution a citrate salt and in another form of the invention the citrate salt solution is a hypertonic solution. The term hypertonic is used herein to refer to a fluid having an osmotic concentration and a density greater than the osmotic concentration and density of the blood of the patient. The antiseptic solution preferably comprises a citrate salt with a concentration range, in weight percent, of from about 1.5% to about 50% with an osmolality of about 300 to about 6400 mOsm. More preferably, the antiseptic solution comprises citrate salt in a concentration range of from about 10% to about 40%, yet more preferably, in a concentration range of from about 20% to about 30%.

In a preferred embodiment, the antiseptic solution is prepared to have a pH lower than that of the pH of the patient's blood. The citrate salt solution may be prepared to have a pH lower than about 6.5, more preferably, from about 4.5 to about 6.5. Also, the citrate salt solution can include pharmaceutically acceptable agents such as sodium chloride and sodium heparin. The citrate salt solution can also include a variety of other antibacterial, antimicrobial and anticoagulant agents such as gentamicin, vancomycin, and mixtures of these agents. Additional anticoagulant agents include, for example heparin, urokinase, tissue plasminogen activation (tPA) and mixtures of these agents.

By "pharmaceutically acceptable," it is meant that the citrate salt solution and the included salts and other additives which are, within the scope of sound medical judgment, suitable for use in contact with tissues of humans and lower animals without undue toxicity, irritation, and allergic response. It is also typically necessary that a composition be sterilized to reduce the risk of infection.

Antibacterial Agent Containing Antiseptic Solutions

An antimicrobial agent containing antiseptic solution of the present invention may contain at least one alcohol, at least one antimicrobial agent and at least one chelator and/or anticoagulant. Various antimicrobial substances as disclosed herein and that are well known to one of ordinary skill in the art may be combined with the locking solution in order to inhibit infection. The antimicrobial locking solution of the present invention may be use for filling or flushing a medical device such as an indwelling device such as an implanted catheter. Other medical devices that are contemplated for use in the present invention are disclosed herein.

In another preferred form of the invention, the antiseptic agent can contain antibacterial agents such as those classified as aminoglycosides, beta lactams, quinolones or fluoroquinolones, macrolides, sulfonamides, sulfamethaxozoles, tetracyclines, treptogramins, oxazolidinones (such as linezolid), clindamycins, lincomycins, rifamycins, glycopeptides, polymxins, lipo-peptide antibiotics, as well as pharmacologically acceptable sodium salts, pharmacologically acceptable calcium salts, pharmacologically acceptable potassium salts, lipid formulations, derivatives and/or analogs of the above.

The aminoglycosides are bactericidal antibiotics that bind to the 30S ribosome and inhibit bacterial protein synthesis. They are typically active against aerobic gram-negative *bacilli* and *staphylococci*. Exemplary aminoglycosides that may be used in some specific aspects of the invention include amikacin, kanamycin, gentamicin, tobramycin, or netilmicin.

Suitable beta lactams are selected from a class of antibacterials that inhibit bacterial cell wall synthesis. A majority of the clinically useful beta-lactams belong to either the penicillin group (penam) or cephalosporin (cephem) groups. The beta-lactams also include the carbapenems (e.g., imipenem), and monobactams (e.g., aztreonam). Inhibitors of beta-lactamase such as clavulanic acid and its derivatives are also included in this category.

Non-limiting examples of the penicillin group of antibiotics that may be used in the solutions of the present invention include amoxicillin, ampicillin, benzathine penicillin G, carbenicillin, cloxacillin, dicloxacillin, piperacillin, or ticarcillin, etc. Examples of cephalosporins include ceftiofur, ceftiofur sodium, cefazolin, cefaclor, ceftibuten, ceftizoxime, cefoperazone, cefuroxime, cefprozil, ceftazidime, cefotaxime, cefadroxil, cephalexin, cefamandole, cefepime, cefdinir, cefriaxone, cefixime, cefpodoximeproxetil, cephapirin, cefoxitin, cefotetan etc. Other examples of beta lactams include mipenem or meropenem which are extremely active parenteral antibiotics with a spectrum against almost all gram-positive and gram-negative organisms, both aerobic and anaerobic and to which *Enterococci, B. fragilis*, and *P. aeruginosa* are particularly susceptible.

Suitable beta lactamase inhibitors include clavulanate, sulbactam, or tazobactam. In some aspects of the present invention, the antibacterial solutions may comprise a combination of at least one beta lactam and at least one beta lactamase inhibitor.

Macrolide antibiotics are another class of bacteriostatic agents that bind to the 50S subunit of ribosomes and inhibit bacterial protein synthesis. These drugs are active against aerobic and anaerobic gram-positive cocci, with the exception of enterococci, and against gramnegative anaerobes. Exemplary macrolides include erythromycin, azithromycin, clarithromycin.

Quinolones and fluoroquinolones typically function by their ability to inhibit the activity of DNA gyrase. Examples include nalidixic acid, cinoxacin, trovafloxacin, ofloxacin, levofloxacin, grepafloxacin, trovafloxacin, sparfloxacin, norfloxacin, ciprofloxacin, moxifloxacin and gatifloxacin.

Sulphonamides are synthetic bacteriostatic antibiotics with a wide spectrum against most gram-positive and many gram-negative organisms. These drugs inhibit multiplication of bacteria by acting as competitive inhibitors of p-aminobenzoic acid in the folic acid metabolism cycle. Examples include mafenide, sulfisoxazole, sulfamethoxazole, and sulfadiazine.

The tetracycline group of antibiotics include tetracycline derivatives such as tigecycline which is an investigational new drug (IND), minocycline, doxycycline or demeclocycline and analogs such as anhydrotetracycline, chlorotetracycline, or epioxytetracycline.

Suitable streptogramin class of antibacterial agents include quinupristin, dalfopristin or the combination of two streptogramins.

Drugs of the rifamycin class typically inhibit DNA-dependent RNA polymerase, leading to suppression of RNA synthesis and have a very broad spectrum of activity against most gram-positive and gram-negative bacteria including *Pseudomonas aeruginosa* and *Mycobacterium* species. An exemplary rifamycin is rifampicin.

Other antibacterial drugs are glycopeptides such as vancomycin, teicoplanin and derivatives thereof. Yet other antibacterial drugs are the polymyxins which are exemplified by colistin.

In addition to these several other antibacterial agents such as prestinomycin, chloramphenicol, trimethoprim, fusidic acid, metronidazole, bacitracin, spectinomycin, nitrofurantion, daptomycin or other leptopeptides, oritavancin, dalbavancin, ramoplamin, ketolide etc. may be used in preparing the antiseptic solutions described herein. Of these, metronidazole is active only against protozoa, such as *Giardia lamblia, Entamoeba histolytica* and *Trichomonas vaginalis*, and strictly anaerobic bacteria. Spectinomycin, is a bacteriostatic antibiotic that binds to the 30S subunit of the ribosome, thus inhibiting bacterial protein synthesis and nitrofurantoin is used orally for the treatment or prophylaxis of UTI as it is active against *Escherichia coli, Klebsiella-Enterobacter* species, *staphylococci*, and *enterococci*.

In other embodiments, the antimicrobial agent is an antifungal agent. Some exemplary classes of antifungal agents include imidazoles or triazoles such as clotrimazole, miconazole, ketoconazole, econazole, butoconazole, omoconazole, oxiconazole, terconazole, itraconazole, fluconazole, voriconazole, posaconazole, ravuconazole or flutrimazole; the polyene antifungals such as amphotericin B, liposomal amphoterecin B, natamycin, nystatin and nystatin lipid formulations; the cell wall active cyclic lipopeptide antifungals, including the echinocandins such as caspofungin, micafungin, anidulfungin, cilofungin; LY121019; LY303366; the allylamine group of antifungals such as terbinafine. Yet other non-limiting examples of antifungal agents include naftifine, tolnaftate, mediocidin, candicidin, trichomycin, hamycin, aurefungin, ascosin, ayfattin, azacolutin, trichomycin, levorin, heptamycin, candimycin, griseofulvin, BF-796, MTCH 24, BTG-137586, pradimicins (MNS 18184), benanomicin; ambisome; nikkomycin Z; flucytosine, or perimycin.

In another preferred form of the invention, the antimicrobial agent is an antiviral agent. Non-limiting examples of antiviral agents include cidofovir, amantadine, rimantadine, acyclovir, gancyclovir, pencyclovir, famciclovir, foscamet, ribavirin, or valcyclovir. In some forms of the invention the antimicrobial agent is an innate immune peptide or proteins. Some exemplary classes of innate peptides or proteins are transferrins, lactoferrins, defensins, phospholipases, lysozyme, cathelicidins, serprocidins, bacteriocidal permeability increasing proteins, amphipathic alpha helical peptides, and other synthetic antimicrobial proteins.

In other embodiments of the invention, the antimicrobial agent is an antiseptic agent. Several antiseptic agents are known in the art and these include a taurinamide derivative, a phenol, a quaternary ammonium surfactant, a chlorine-containing agent, a quinaldinium, a lactone, a dye, a thiosemicarbazone, a quinone, a carbamate, urea, salicylamide, carbanilide, a guanide, an amidine, an imidazoline biocide, acetic acid, benzoic acid, sorbic acid, propionic acid, boric acid, dehydroacetic acid, sulfurous acid, vanillic acid, esters of p-hydroxybenzoic acid, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5, 7-triazo 1-azoniaadamantane chloride, taurolidine, taurultam, N(5-nitro-2-furfurylidene)-1-amino-hydantoin, 5-nitro-2-furaldehyde semicarbazone, 3,4,4'-trichlorocarbanilide, 3,4',5-tribromosalicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, or silver nitrate.

In another preferred form of the invention, the antiseptic solution includes a basic reagent and a dye. The basic reagent may be a guanidium compound, a biguanide, a bipyridine, a phenoxide antiseptic, an alkyl oxide, an aryl oxide, a thiol, a halide, an aliphatic amine, or an aromatic amine. In some specific aspects, the basic reagent is a guanidium compound. Non-limiting examples of guanidium compounds include chlorhexidine, alexidine, hexamidine. In other specific embodiments, the basic reagent is a bipyridine. One example of a bipyridine is octenidine. In yet other aspects, the basic reagent is a phenoxide antiseptic.

The dye may be a triarylmethane dye, a monoazo dye, a diazo dye, an indigoid dye, a xanthene dye, an anthraquinone dye, a quinoline dye, an FD&C dye. Non-limiting examples of triarylmethane dye include gentian violet, crystal violet, ethyl violet, or brilliant green. Exemplary monoazo dyes include FD&C Yellow No. 5, or FD&C Yellow No. 6. Other non-limiting examples of FD&C dye include Blue No. 1 or Green No. 3. One non-limiting example of diazo dyes is D&C Red No. 17. An example of an indigoid dye is FD&C Blue No. 2. An example of a xanthene dye is FD&C Red No. 3; of an anthraquinone dye is D&C Green No. 6; and of an quinoline dye is D&C Yellow No. 1.

Other examples of antiseptics that may be used to the solutions of the invention are the phenoxide antiseptics such as clofoctol, chloroxylenol or triclosan. Still other antiseptic agents that may be used to prepare the amntimicrobial solutions of the invention are gendine, genlenol, genlosan, or genfoctol.

One of skill in the art will appreciate that one can use one or more of the antimicrobial agents including one or more antibacterial agent, and/or one or more antifungal agent, and/or one or more antiviral agent, and/or one or more antiseptic agent, and/or combinations thereof A wide variety of chelator agents are contemplated as useful in preparing the antiseptic solutions of the invention. This includes chelators such as EDTA free acid, EDTA 2Na, EDTA. 3Na, EDTA 4Na, EDTA 2K, EDTA 2Li, EDTA 2NH4, EDTA 3K, Ba(II)-EDTA, Ca(II)-EDTA, Co(II)-EDTACu(II)-EDTA, Dy(III)-EDTA, Eu(III)-EDTA, Fe(III)-EDTA, In(III-EDTA, La(III)-EDTA, CyDTA, DHEG, diethylenetriamine penta acetic acid (DTPA), DTPA-OH, EDDA, EDDP, EDDPO, EDTA-OH, EDTPO, EGTA, HBED, HDTA, HIDA, IDA, MethylEDTA, NTA, NTP, NTPO, O-Bistren, TTHA, EGTA, DMSA, deferoxamine, dimercaprol, zinc citrate, a combination of bismuth and citrate, penicillamine, succimer or Etidronate. It is contemplated that any chelator which binds barium, calcium, cerium, cobalt, copper, iron, magnesium, manganese, nickel, strontium, or zinc will be acceptable for use in the present invention.

Alternatively, one may use at least one anticoagulant such as heparin, hirudin, EGTA, EDTA, urokinase, streptokinase, hydrogen peroxide etc., in the preparation of the antimicrobial solutions of the invention.

In addition to the alcohols set forth above, a variety of alcohols are contemplated as useful in the preparation of the instant antiseptic solution, and include any antimicrobially active alcohol. Non-limiting examples of alcohols include ethanol, methanol, isopropanol, propylene glycol, benzyl alcohol, chlorobutanol, phenylethyl alcohol, and the like.

One of skill in the art will appreciate that the solutions of the instant invention can comprise various combinations of at least one alcohol, at least one antimicrobial agent, and at least one chelator/anticoagulant. In some specific embodiments, the solution of the invention comprises at least one alcohol, at least one tetracycline and at least one chelator/anticoagulant. In a specific aspect, such an antimicrobial solution comprises ethanol, at least one tetracycline and EDTA or heparin.

In other specific aspects, such a solution comprises ethanol, minocycline and EDTA or heparin. In one embodiment of this aspect, the concentration of minocycline is 0.001 mg/ml to 100 mg/ml. In another embodiment, the concentration of minocycline is about 3 mg/ml. In another aspect, the concentration of EDTA is in the range of 10-100 mg/ml. In one embodiment of this aspect, the concentration of EDTA is about 30 mg/ml.

In another preferred form of the invention, the antiseptic solution includes a pharmacologically acceptable sodium salt, a pharmacologically acceptable calcium salt, a pharmacologically acceptable potassium salt and about one milligram per milliliter polyhexamethylene biguanide hydrochloride in an aqueous admixture. Additionally, the solution of the invention may also contain a pharmacologically acceptable salt of lactic acid.

Salt Containing Antiseptic Solutions

One preferred antiseptic solution includes a pharmacologically acceptable sodium salt such as sodium chloride or the like in a concentration of between about 820 mg to about 900 mg, a pharmacologically acceptable calcium salt, such as calcium chloride dihydrate or the like in a concentration between about 30.0 mg to about 36.0 mg, a pharmacologically acceptable potassium salt, such as potassium chloride or the like in a concentration between about 28.5 to about 31.5 mg and about one milligram per milliliter polyhexamethylene biguanide hydrochloride in an aqueous admixture with one hundred milliliters of water for injection U.S.P. For particular applications, the solution of the invention may also include sodium lactate in a concentration between about 290 mg and about 330 mg in the one hundred milliliter aqueous admixture.

Photo-Oxidant Solutions

In another preferred form of the present invention, the antiseptic solution contains an anticoagulant and a photo-oxidant. In certain embodiments, a photo-oxidant is selected that has an antiseptic effect. As used herein, the term "photo-oxidant" is intended to refer to a compound (usually an organic dye) that has photo-oxidation properties, in which the compound exhibits an increased oxidizing potential upon exposure to radiant energy such as light. The term "photooxidant" also refers to a composition that releases one or more electrons when struck by light.

In one preferred aspect of the invention, the photo-oxidant is methylene blue, which advantageously provides antibiotic and antifungal activity, and also provides a color to make the antiseptic solution clearly identifiable. In addition to methylene blue, other photo-oxidants may include Rose Bengal, hypericin, methylene violet, proflavine, rivanol, acriflavine, toluide blue, trypan blue, neutral red, a variety of other dyes or mixtures thereof. Therefore, in alternate aspects of the invention, one or more alternative photo-oxidants, preferably a colored photo-oxidant is used in accordance with the invention in place of methylene blue.

Enhanced Viscosity Solutions

In another preferred form of the invention, the antiseptic solution includes a low viscosity antibacterial agent mixed with a viscosity increasing agent. Examples of antibacterial agents which may be used, in addition to those described above, comprise alcohols, chlorhexidine, Chlorpactin, iodine, tauroline, citric acid, and soluble citric acid salts, particularly sodium citrate, optionally mixed with water.

Suitable viscosity increasing agents include Carbopol, starch, methylcellulose, carboxypolymethylene, carboxymethyl cellulose, hydroxypropylcellulose, or the like. Carbopol is a cross-linked polyacrylic acid based polymer sold by Noveon, Inc. It is preferably neutralized to about pH 7 with a base material such as tetrahydroxypropyl ethylene diamine, triethanolamine, or sodium hydroxide. Derivatives of starch may also be used, such as hydroxyethylstarch, hydroxypropylstarch, or starch having bonded organic acid ester groups, to improve compatibility with antibacterial agents such as alcohols, for example, ethanol or isopropanol. Such ester groups may be the reaction product of two to twelve carbon organic acids with the starch, for example. Also, the elevated viscosity antiseptic solution may be created by the use of a fat emulsion, or other dispersions in water/alcohol of glycerol mono or di esters of fatty acids, or fatty acid esters of other polyols such as sugars having one or more bonded fatty acid groups per molecule. Analogous compounds with ether linkages may also be used.

Also, other materials such as alginic acid, with or without calcium citrate may be used, or polyvinyl alcohol, with or without borax, povidone, polyethylene glycol alginate, sodium alginate, and/or tragacanth. If desired, the fluid of this invention may also contain an effective amount of an antithrombogenic agent such as heparin, and a diluent such as water, along with other desired ingredients.

In one preferred form of the invention, the antiseptic solution contains a mixture of isopropyl alcohol and neutralized Carbopol, with other optional ingredients being present such as water, antithrombogenic agents such as heparin, and the like. Preferably, about 0.4 to 2 weight percent of Carbopol is present. Citric acid may also be present as an antibacterial agent, either with or as a substitute for another anti-bacterial agent such as isopropyl alcohol or ethanol.

In another embodiment, the antiseptic solution is a gel of an isopropyl alcohol, optionally with up to about 30 weight percent water, and about 2.2 weight percent hydroxypropylcellulose, to form a high viscosity antiseptic solution.

In yet another preferred form of the invention, the antiseptic solution contains carbohydrates and/or glucose degradation products. Suitable carbohydrates are chosen form the group of glucose and/or fructose. Suitable degradation products include 3-deoxyglucosone (3-DG), acetaldehyde, formaldehyde, acetaldehyde, glyoxal, methylglyoxal, 5-hydroxymethyl-2-furaldehyde (5-HMF), 2-furaldehyde, and 3,4-dideoxyglucosone-3-ene (3,4-DGE).

Other suitable agents to be used in this embodiment of the antiseptic solution includes substances having anticoagulatory properties i.e., inhibitors of the coagulation cascade such as heparin of standard and low molecular weight, fractionated heparin, synthetic inhibitors in the coagulation cascade, Futhan as a broad protease inhibitor, complexing and chelating substances such as citrate, EDTA, EGTA, substances and mixtures used for preservation of blood products (platelets or plasma), CDPA (citrate, sodium phosphate, dextrose, adenine), synthetic or natural thrombin inhibitor substances. Other suitable additives include fucosidan, riboflavin, vitamin E, alphatocopherol, folic acid and amino acids. Furthermore, antiinflammatory compounds and drugs could also be used, e.g. cortison, mycophenolic acid (MPA) and derivates thereof, sirolimus, tacrolimus and cyclosporin, diclofenac, etc.

Inhibitory peptides can also be used in the antiseptic solution such as defensins, (dermacidine), and others. Radicals, such as reactive oxygene species, NO-releasing systems or nitric oxide (NO), and peroxynitrite may also be used. A buffer composition may also be included in the antiseptic solution, and in one preferred form of the invention, the buffer contains lactate, bicarbonate, pyruvate, ethyl pyruvate and citric acid in combination and mixtures including adjustment of pH by acetic acid, hydrochloric acid or sulphuric acid. Furthermore, viscosity enhancing additives may be added, such as lipids or lipidic substances (also to get water insoluble vitamins or complexes into solution), nutrients in high concentration density gradient e.g. aminoacid containing fluids, polyglucose, Icodextrin, pectine, hydroxyethyl starch (HES), alginate, hyaluronic acid, etc.

Taurolidine Antiseptic Solutions and Gels

The antiseptic solutions of the present invention can include Taurolidine and/or Taurultam to prevent clotting and Biofilm formation or the elements can be combined with other antimicrobial agents. One embodiment of the present invention is a gel with thixotropic properties to keep the solution inside the antiseptic cap and not spill out during the time interval between uses. This is accomplished by making a hydrogel matrix as a drug delivery vehicle containing a biocompatible antimicrobial agent alone or with another active agent, which may be useful for particular purposes. The hydrogel matrix is biocompatible and, biodegradable in the bloodstream. The matrix can be a hydrogel (e.g., pectin, gelatin, etc), a protein (e.g., collagen, hemoglobin, etc), a colloidal substance (e.g., serum albumin etc.), an emulsion or other adjuvant. Preferably, the matrix shall have structural integrity and be thixotropic. Thixotropy is a property, which is exhibited by certain gels. It is a property characterized by a solid or semisolid substance that when shaken, stirred or subject to high shear forces becomes fluid like and can flow and then returns to the semisolid state when the forces and/movement are stopped. Alternatively, the gel could have the properties similar to that of the colloidal dispersion which resists movement, or flow until a high shear force is imparted to the fluid and then it flows easily.

Other ingredients may be added to the gel matrix to provide further functional benefit. The preferred antimicrobial is Taurolidine, which can be added to the matrix as a micro particle powder, or encapsulated in liposomes, microspheres, or nanospheres. It should be appreciated that numerous active agents and drugs can be added to the thixotropic gel including sterileants, lysing agents (such as Urokinase), imaging enhancers, catheter surface modifiers, antibiotics and antimicrobial chemicals.

A hydrogel comprises a three-dimensional molecular network containing large quantities of water giving them good biocompatibility with material consistency that is soft solid-like with high diffusive properties to gases, chemicals and proteins. Suitable hydrogels include natural polymers including serum albumin, collagen, or alginates, polyvinyl alcohol, poly (ethylene oxide) or poly (hydroxyethylene) and polyelectrolytes, such as poly(acrylic acid), poly(styrene sulfonate), and carboxymethylcellulose (CMC).

One preferred form of the antiseptic solution includes Taurolidine with Salicylic acid or Sodium Salicylate in an aqueous solvent. Salicylic Acid and Sodium Salicylate are drugs that have been used with antibiotic locks in catheters to enhance the biocidal action of the antibiotic alone and to inhibit the attachment of microbes to surfaces. This last attribute is especially important because the initiation of a Biofilm expression and growth require that the individual bacteria must first attach themselves to the underlying surface. By stopping attachment, Biofilm formation is blocked.

Sodium salicylate has been demonstrated to have remarkable antibacterial activity, including the ability to enhance the activities of certain antibiotics. This drug inhibits adherence, growth and Biofilm formation.

EDTA Containing Antiseptic Solutions

In one preferred antiseptic solution of the present invention provides antimicrobial, antifungal, anti-viral and anti-amoebic properties and may also serve as an anti-coagulant. Specified salts and compositions of ethylene diamine tetraacetic acid (EDTA) ($C_{10}H_{12}N_2Na_4O_8$) are used at specified concentrations and pH levels.

The EDTA formulations of the present invention are safe for human administration and are biocompatible and non-corrosive. They may also have anticoagulant properties and are thus useful for preventing and/or treating a variety of catheter-related infections. In one embodiment, antiseptic solutions of the present invention have at least four, and preferably at least five, of the following properties: anticoagulant properties; inhibitory and/or bactericidal activity against a broad spectrum of bacteria in a planktonic form; inhibitory and/or fungicidal activity against a spectrum of fungal pathogens; inhibitory and/or bactericidal activity against a broad spectrum of bacteria in a sessile form; inhibitory activity against protozoan infections; inhibitory activity against Acanthamoeba infections; safe and biocompatible, at least in modest volumes, in contact with a patient; safe and biocompatible, at least in modest volumes, in a patient's bloodstream; and safe and compatible with industrial objects and surfaces. The antiseptic solution can have a pH higher than physiological pH such as a pH of >8.0, or at a pH >8.5, or at a pH>9, or at a pH>9.5.

In another preferred form of the invention, the antiseptic solution contain a sodium EDTA salt (or combination of sodium salts) in solution at a pH in the range between 8.5 and 12.5 and, in another embodiment, at a pH of between 9.5 and 11.5 and, in yet another embodiment, at a pH of between 10.5 and 11.5.

When used herein, the term "EDTA salt" may refer to a single salt, such as a di-sodium or tri-sodium or tetra-sodium salt, or another EDTA salt form, or it may refer to a combination of such salts. The composition of EDTA salt(s) depends both on the EDTA salts used to formulate the composition, and on the pH of the composition. For antiseptic solutions of the present invention consisting of sodium EDTA salt(s), and at the desired pH ranges (specified above), the sodium EDTA salts are predominantly present in both the tri-sodium and tetra-sodium salt forms.

In one embodiment, the antiseptic solution contains a combination of at least the tri-sodium and tetra-sodium salts of EDTA, and more preferably solutions containing at least 10% of the EDTA in the composition is present in the tetra-sodium salt form. In yet another embodiment, at least 50% and, more preferably at least 60%, of the EDTA in the composition is present in the tri-sodium salt form.

EDTA solutions of the present invention are preferably provided in a sterile and non-pyrogenic form and may be packaged in any convenient fashion. The compositions may be prepared under sterile, aseptic conditions, or they may be sterilized following preparation and/or packaging using any of a variety of suitable sterilization techniques.

Formulation and production of antiseptic compositions of the present invention is generally straightforward. In one embodiment, desired antiseptic solutions of the present invention are formulated by dissolving one or more EDTA salt(s) in an aqueous solvent, such as purified water, to the desired concentration and adjusting the pH of the EDTA salt solution to the desired pH. The antiseptic solution may then be sterilized using conventional means, such as autoclaving, UV irradiation, filtration and/or ultrafiltration, and other means. The preferred osmolarity range for EDTA solutions is from 240-500 mOsM/Kg, more preferably from 300-420 mOsm/Kg. The solutions are preferably formulated using USP materials.

Antiseptic solutions containing sodium salts of EDTA other than tri- and tetra-sodium salts, such as di-sodium EDTA, is also contemplated. For example di-sodium EDTA solutions can be used but such solutions have a lower pH in solution than the desired pH range of compositions of the present invention but, upon pH adjustment to the desired range using a pH adjustment material, such as sodium hydroxide, sodium acetate, and other well-known pH adjustment agents, EDTA solutions prepared using di-sodium salts are converted to the preferred combination di- and/or tri- and/or tetra-sodium salt EDTA solutions of the present invention. Thus, different forms and combinations of EDTA salts may be used in the preparation of EDTA compositions of the present invention, provided that the pH of the composition is adjusted to the desired pH range prior to use. In one embodiment, antiseptic compositions consisting of a mixture of primarily tri-and tetra-sodium EDTA is provided by dissolving di-sodium EDTA in an aqueous solution, 3%-5% on a weight/volume basis, and adding sodium hydroxide in a volume and/or concentration sufficient to provide the desired pH of>8.5 and <12.0.

Antibacterial Enzyme Containing Antiseptic Solutions

"Antibacterial enzyme" refers to any proteolytic, pore-forming, degradative or inhibitory enzyme that kills or damages a bacterial species or particular strain thereof The result may be achieved by damaging the cell wall of the bacteria, disrupting cell membranes associated with the cell wall or within the bacteria, inhibiting protein synthesis within the bacteria, disrupting the sugar backbone, or by any other mechanism attributed to a peptide or protein considered by those skilled in the art to be an antibacterial enzyme. The enzyme may be a natural, wild-type enzyme, modified by conventional techniques, conjugated to other molecules, recombinantly expressed, or synthetically constructed.

One example of an antibacterial enzyme is lysostaphin. Lysostaphin is important because it is effective in the treatment of staphylococci and biofilms formed therefrom. "Lysostaphin," and "lysostaphin analogues" are defined as including lysostaphin (wild type), any lysostaphin mutant or variant, any recombinant, or related enzyme (analogue) or any synthetic version or fragment of lysostaphin (whether synthetic or otherwise) that retains the proteolytic ability, in vivo and in vitro, to cleave the cross-linked polyglycine bridges in the cell wall peptidoglycan of staphylococci. The enzymes may be generated by post-translational processing of the protein (either by enzymes present in a producer strain or by means of enzymes or reagents introduced at any stage of the process) or by mutation of the structural gene. Mutations may include site deletion, insertion, domain removal and replacement mutations.

The lysostaphin may be synthetically constructed, expressed in mammalian cells, insects, bacteria, yeast, reptiles or fungi, recombinantly expressed from a cell culture or higher recombinant species such as a mouse, or otherwise. This would include the activity-retaining synthetic construction including synthetic peptides and polypeptides or recombinant expression of portions of the lysostaphin enzyme responsible for its activity against staphylococci as part of a larger protein or peptide, include chimeric proteins, containing the active sites of one or more other antibacterial enzymes that are effective either against staphylococci or other biofilmforming bacteria species.

The antibacterial enzymes may also be coated on the surface of the devices described herein by immersion of the device in a solution of the enzyme for a length of time sufficient to form a biofilm-formation inhibiting coating of the enzyme on the susceptible surface. Even the most minimal concentration of enzyme will confer some protection. Typically, a concentration of from about 10 µg/ml to about 100 mg/ml can be used. With device surfaces, the coatings may also be formed by covalent attachment of the enzyme thereto.

Antiseptic Coatings

It is contemplated that the devices described herein can be coated with an antiseptic coating by any suitable technique such as immersion of the part into an antiseptic solution, by spray coating the part with the antiseptic solution, by blending the antiseptic solution or material into the polymeric material used to fabricate the device.

In one preferred form of the invention, a quantity of physiological, antimicrobial metal compound is added to the resin for direct molding of an article. Physiological, antimicrobial metals are meant to include the precious metals, such as silver, gold and platinum, and copper and zinc. Physiological, antimicrobial metal compounds used herein include oxides and salts of preferably silver and also gold, for example: silver acetate, silver benzoate, silver carbonate, silver citrate, silver chloride, silver iodide, silver nitrate, silver oxide, silver sulfa diazine, silver sulfate, gold chloride and gold oxide. Platinum compounds such as chloroplatinic acid or its salts (e.g., sodium and calcium chloroplatinate) may also be used. Also, compounds of copper and zinc may be used, for example: oxides and salts of copper and zinc such as those indicated above for silver. Single physiological, antimicrobial metal compounds or combinations of physiological, antimicrobial metal compounds may be used.

Preferred physiological, antimicrobial metal compounds used in this invention are silver acetate, silver oxide, silver sulfate, gold chloride and a combination of silver oxide and gold chloride. The particles of the silver compounds are sufficiently able to be extracted to form a zone of inhibition to prevent and kill bacteria growth.

In another preferred form of the invention the devices herein are impregnated with triclosan and silver compounds or triclosan and chlorhexidine.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed is:

1. A method of cleaning and covering an access site, the method comprising the steps of:
    flushing an access site with a solution;
    storing a container and a threaded cap in a syringe;
    removing a sealing cover on the container having the threaded cap, the threaded cap having an antiseptic fluid therein;
    threading the cap onto the access site with the cap positioned in the container, the cap including a sponge and the antiseptic fluid being retained in the sponge, the sponge contacting the access site when the cap is threaded onto the access site;
    withdrawing the cap from the container; and
    allowing the cap to remain on and cover the access site.

2. The method of claim 1 further comprising the step of removing the container and the cap from the syringe after engaging the cap with the access site.

3. The method of claim 2 further comprising the step of retaining antiseptic fluid within the cap by sealing the cap with a thread cover engaging the access site.

4. The method of claim 3, wherein the step of threading the cap onto the access site with the cap positioned in the container includes the step of preventing relative rotational movement between the syringe and the cap to ensure common rotational movement about a common axis.

5. The method of claim 4, wherein the step of flushing an access site with a solution comprises flushing an access site with a solution delivered by a syringe.

6. A method of cleaning and covering an access site, the method comprising the steps of:
    flushing an access site with a solution;
    storing a threaded cap in a syringe, the threaded cap having an antiseptic fluid therein;
    threading the cap onto the access site; and
    allowing the cap to remain on and cover the access site by moving the syringe away from the access site.

7. The method of claim 6, wherein the threaded cap is provided in a container.

8. The method of claim 7, further comprising the step of withdrawing the cap from the container.

9. The method of claim 8, wherein the cap includes a sponge and the antiseptic fluid is retained in the sponge, the sponge contacting the access site when the cap is threaded on the access site.

10. The method of claim 9 further comprising the step of retaining antiseptic fluid within the cap by sealing the cap with a thread cover engaging the access site.

11. The method of claim 10, wherein the step of threading the cap onto the access site includes the step of preventing relative rotational movement between the syringe and the cap to ensure common rotational movement about a common axis.

12. A method of cleaning and covering an access site, the method comprising the steps of:
    flushing an access site with a solution delivered by a syringe;
    removing a sealing cover on a container having a threaded cap with a thread cover, the threaded cap having an antiseptic fluid therein;
    threading the cap onto the access site with the cap positioned in the container, the cap including a sponge and the antiseptic fluid being retained in the sponge, the sponge contacting the access site when the cap is threaded onto the access site;
    withdrawing the container from the cap;
    allowing the cap to remain on and cover the access site, thereby retaining antiseptic fluid within the cap; and
    storing the container and the cap in a second syringe.

13. The method of claim 12 further comprising the step of removing the container and the cap from the second syringe after engaging the cap with the access site.

* * * * *

UNITED STATES PATENT AND TRADEMARK OFFICE
CERTIFICATE OF CORRECTION

PATENT NO. : 8,231,602 B2  
APPLICATION NO. : 13/095516  
DATED : July 31, 2012  
INVENTOR(S) : William Anderson Page 1 of 1

It is certified that error appears in the above-identified patent and that said Letters Patent is hereby corrected as shown below:

On Title page 2, Item (56), under the continuation of references cited, "635,344" should be --7,635,344--;

Column 7, line 5, "than" should be --then--;

Column 17, line 30, "amntimicrobial" should be --antimicrobial--;

Column 17, line 42, "2NH4" should be --2NH$_4$--;

Column 22, line 28, after "thereof" insert --.--.

Signed and Sealed this  
Fifth Day of February, 2013

Teresa Stanek Rea  
*Acting Director of the United States Patent and Trademark Office*